United States Patent
Llull et al.

(10) Patent No.: US 9,907,883 B2
(45) Date of Patent: *Mar. 6, 2018

(54) METHOD FOR PROCESSING CANCELLOUS BONE MATERIAL AND RELATED PRODUCTS, METHODS AND USES

(71) Applicant: THE GID GROUP, INC., Louisville, CO (US)

(72) Inventors: Ramon Llull, Palma de Mallorca (ES); Severiano Dos Anjos Vilaboa, Palma de Mallorca (ES); William W. Cimino, Louisville, CO (US)

(73) Assignee: The GID Group, Inc., Louisville, CO (US)

( * ) Notice: Subject to any disclaimer, the term of this patent is extended or adjusted under 35 U.S.C. 154(b) by 274 days.

This patent is subject to a terminal disclaimer.

(21) Appl. No.: 14/440,846

(22) PCT Filed: Jan. 10, 2014

(86) PCT No.: PCT/US2014/011152
§ 371 (c)(1),
(2) Date: May 5, 2015

(87) PCT Pub. No.: WO2014/110448
PCT Pub. Date: Jul. 17, 2014

(65) Prior Publication Data
US 2015/0359941 A1    Dec. 17, 2015

Related U.S. Application Data

(60) Provisional application No. 61/751,736, filed on Jan. 11, 2013.

(51) Int. Cl.
*A61L 27/36* (2006.01)
*A61K 35/32* (2015.01)
(Continued)

(52) U.S. Cl.
CPC .......... *A61L 27/3683* (2013.01); *A61K 35/32* (2013.01); *A61L 27/20* (2013.01);
(Continued)

(58) Field of Classification Search
None
See application file for complete search history.

(56) References Cited

U.S. PATENT DOCUMENTS

| 3,854,704 A | 12/1974 | Balas |
| 9,206,387 B2 | 12/2015 | Llull et al. |

(Continued)

FOREIGN PATENT DOCUMENTS

| WO | 2007133451 A1 | 11/2007 |
| WO | 2009125402 A2 | 10/2009 |

(Continued)

OTHER PUBLICATIONS

Bones: Structure and Mechanics. Cancellous bone. Princeton University Press (publisher). Copyright 2002. Princeton University Press. Princeton, New Jersey. pp. 21-23.*

(Continued)

*Primary Examiner* — Renee Claytor
*Assistant Examiner* — Sharon M. Papciak
(74) *Attorney, Agent, or Firm* — Marsh Fischmann & Breyfogle LLP

(57) ABSTRACT

Cancellous bone material may be processed in a portable container apparatus to prepare a stromal vascular fraction concentrate. Cancellous bone material may be washed to remove non-bone material, digested and digested material centrifuged, with all operations being performed on cancellous bone material while disposed in the portable container apparatus. Uncultured stromal vascular fraction cells separated from enzyme-digested cancellous bone material, and which contain osteoblasts and osteoclasts, may be removed (Continued)

from the portable container and used without culturing for a variety of medical applications. Medical treatment compositions may be prepared including recovered stromal vascular fraction cells and scaffold material.

18 Claims, 24 Drawing Sheets

(51) Int. Cl.
*A61L 27/20* (2006.01)
*A61L 27/38* (2006.01)
*A61L 27/54* (2006.01)
*C12M 1/00* (2006.01)
*C12N 5/071* (2010.01)
*A61L 27/22* (2006.01)
*C12N 5/0775* (2010.01)

(52) U.S. Cl.
CPC .......... *A61L 27/225* (2013.01); *A61L 27/365* (2013.01); *A61L 27/3608* (2013.01); *A61L 27/3616* (2013.01); *A61L 27/3804* (2013.01); *A61L 27/3821* (2013.01); *A61L 27/3847* (2013.01); *A61L 27/54* (2013.01); *C12M 45/09* (2013.01); *C12N 5/0663* (2013.01); *A61L 2300/414* (2013.01); *A61L 2430/02* (2013.01); *C12N 2509/00* (2013.01)

(56) References Cited

U.S. PATENT DOCUMENTS

| | | |
|---|---|---|
| 9,260,697 B2 | 2/2016 | Cimino et al. |
| 9,296,984 B2 | 3/2016 | Cimino et al. |
| 2008/0319417 A1 | 12/2008 | Quijano et al. |
| 2010/0055087 A1 | 3/2010 | Higgins et al. |
| 2010/0124563 A1 | 5/2010 | Coleman et al. |
| 2012/0003733 A1 | 1/2012 | Gueneron |
| 2013/0164731 A1 | 6/2013 | Cimino et al. |
| 2014/0363891 A1 | 12/2014 | Llull et al. |
| 2015/0118752 A1 | 4/2015 | Cimino et al. |

FOREIGN PATENT DOCUMENTS

| | | |
|---|---|---|
| WO | 2012006587 A2 | 1/2012 |
| WO | 2015035221 A1 | 3/2015 |

OTHER PUBLICATIONS

NCI Drug Dictionary. Stromal vascular fraction. Datasheet [online]. NIH, NCI [retrieved on Jun. 14, 2017] Retrieved from the Internet: <URL: http://www.cancer.gov/publications/dictionaries/cancer-drug?cdrid=777203>.*
Sakaguchi, et al. Suspended Cells From Trabecular Bone by Collagenase Digestion Become Virtually Identical to Mesenchymal Stem Cells Obtained From Marrow Aspirates. Blood (2004) vol. 104, No. 9, pp. 2728-2735.
Williams, et al. Stem Cells From Viable Cancellous Bone Demonstrate Multilineage Differentiation and Characteristic Cell Surface Markers. Abstract, American Association of Tissue Banks 29th Annual Meeting (2005).
Tuli, et al. Characterization of Multipotential Mesenchymal Progenitor Cells Derived From Human Trabecular Bone. Stem Cells (2003) vol. 21, pp. 681-693.
Tuli, et al. A Simple, High-Yield Method for Obtaining Multipotential Mesenchymal Progenitor Cells From Trabecular Bone. Molecular Biotechnolgy (2003) vol. 23, pp. 37-49.
Suire, et al. Isolation of the Stromal-Vascular Fraction of Mouse Bone Marrow Markedly Enhances the Yield of Clonogenic Stromal Progenitors. Blood (2012) vol. 119, No. 11, pp. e86-e95.
Pendleton, et al. Mesenchymal Stem Cells Derived From Adipose Tissue vs Bone Marrow: In Vitro Comparison of Their Tropism Towards Gliomas. PLoS ONE (2013) vol. 8, Issue 3, e58198. 7 pages.
Noth, et al. Multilineage Mesenchymal Differentiation Potential of Human Brabecular Bone-Derived Cells. Journal of Orthopaedic Research (2002) vol. 20, pp. 1060-1069.
Gupta, et al. Mesenchymal Stem Cells for Cartilage Repair in Osteoarthritis. Stem Cell Research & Therapy (2012), 3:25, 9 pages.
Jones, et al. Large-Scale Extraction and Characterization of CD271+ Multipotential Stromal Cells From Trabecular Bone in Health and Osteoarthritis. Arthritis & Rheumatism (2010) vol. 62, No. 7, pp. 1944-1954.
Centeno, et al. Increased Knee Cartilage Volume in Degenerative Joint Disease Using Percutaneously Implanted, Autologous Mesenchymal Stem Cells. Pain Physician (2008)11:3, pp. 343-353. ISSN 1533-3159.
Al-Nbaheen, et al. Human Stromal (Mesenchymal) Stem Cells From Bone Marrow, Adipose Tissue and Skin Exhibit Differences in Molecular Phenotype and Differentiation Potential. Stem Cell Rev and Rep (2013) vol. 9, pp. 32-43 (Published Online Apr. 14, 2012.).

* cited by examiner

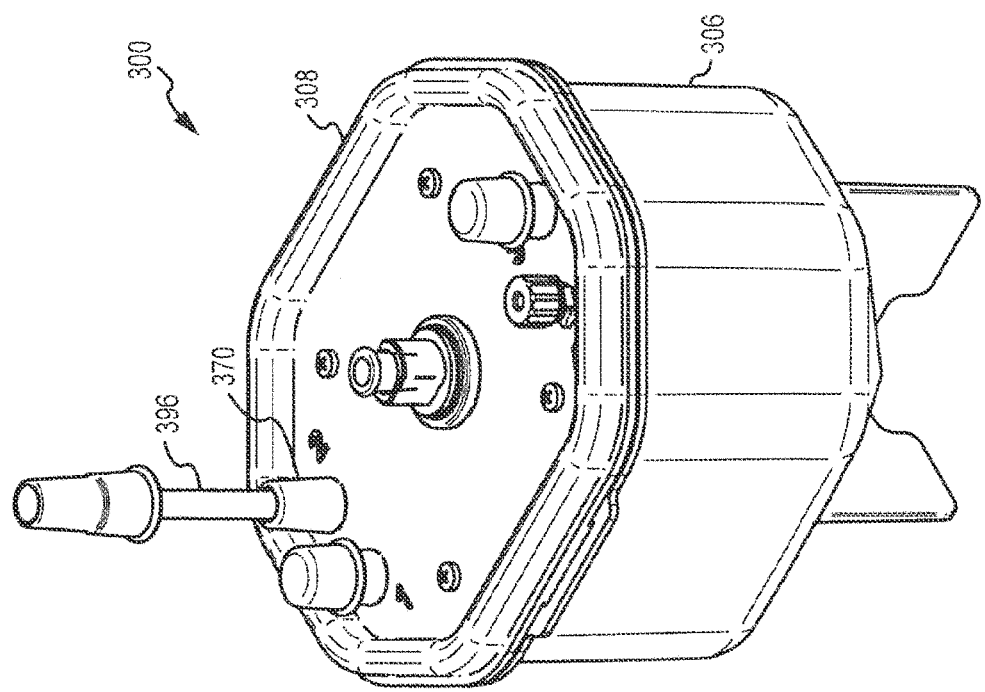

METHOD FOR PROCESSING CANCELLOUS BONE MATERIAL AND RELATED PRODUCTS, METHODS AND USES

REFERENCE TO U.S. APPLICATIONS

This application claims the benefit of U.S. provisional patent application No. 61/751,736 filed Jan. 11, 2013, the entire contents of which are incorporated by reference herein as if set forth herein in full.

FIELD OF THE INVENTION

The invention relates to methods and apparatus related to processing cancellous bone material, for example to prepare a concentrate with stromal vascular fraction cells, apparatus for use in the processing and compositions, products and methods including stromal vascular fraction cells from enzyme-digested cancellous bone material.

BACKGROUND OF THE INVENTION

Cancellous bone, also known as spongy bone or trabecular bone, is a softer, less dense bone that occurs at many locations in the human body, for example within the interior or at the ends of various bones and in the vicinity of bone joints. Non-bone tissue associated with cancellous bone may include vascular material, such as bone marrow and blood. Bone marrow has long been recognized as a source of mesenchymal stem cells, and bone marrow has been extracted and processed by centrifuging techniques to prepare a fraction enriched in such stem cells relative to the in-tact bone marrow. Cancellous bone and associated tissue may also be processed to recover mesenchymal stem cells. Cancellous bone and associated tissue have been subjected to collagenase digestion to remove soft tissue components associated with bone surfaces and resulting bone fragments have been cultured as explants to expand such stem cells for possible beneficial use. Collagenase-released cells from such digestion have also been cultured to expand the stem cells for possible beneficial use. These cultured cells represent a potential source of stem cells in larger numbers than obtainable by concentrating stem cells from bone marrow, and which would be useful for a variety of therapeutic applications. However, such culturing has traditionally involved a laborious and time-consuming procedure, and limits practical utility of cancellous bone and associated tissue as a source for stem cells.

SUMMARY OF THE INVENTION

With careful processing of cancellous bone material, stromal vascular fraction concentrate may be prepared and recovered with sufficient numbers and concentrations of stromal vascular fraction cells, including stem cells, for advantageous use for a variety of medical applications without a need to culture the cells.

A first aspect of the disclosure is provided by a method for processing cancellous bone material. The cancellous bone material may initially include cancellous bone and associated non-bone material. The method permits preparation of a concentrate rich in stromal vascular fraction cells (also referred to as stromal vascular cells or as leuko stromal vascular cells) originally contained in cancellous bone material. The method includes multi-step processing performed using a portable container apparatus. The portable container apparatus has a filter disposed in an internal containment volume of the portable container apparatus and the internal containment volume includes a retentate volume (also referred to herein as a tissue retention volume) on one side of the filter and a filtrate volume on another side of the filter. The processing may include washing, comprising adding aqueous wash liquid to the portable container apparatus to contact cancellous bone material disposed within the retentate volume and removing from the filtrate volume at least a majority of the aqueous wash liquid together with at least some non-bone constituents washed from the cancellous bone material. The processing may include, after the washing, digesting, with the digesting comprising adding to the portable container apparatus a digestion medium comprising collagenase enzyme to contact the digestion medium with at least a washed portion of the cancellous bone material disposed in the retentate volume. The multi-step processing may include, after the digesting, centrifuging the portable container apparatus having disposed within the internal containment volume at least a digested portion of the cancellous bone material, and during the centrifuging forming in the internal containment volume of the portable container apparatus density-separated phases including lower-density material phases and a higher-density pellet phase concentrated in stromal vascular fraction cells from the cancellous bone material.

A number of feature refinements and additional features are applicable to the first aspect of the disclosure. These feature refinements and additional features may be used individually or in any combination. As such, each of the following features may be, but are not required to be, used with any other feature or combination of the first aspect or other aspects of the disclosure.

The method may include one or more steps in addition to the steps noted above. Any such additional step may be performed between any of the steps noted above or may be performed before a first step or after a last step in sequence of any of the steps noted above.

The processing of the method may include, after the centrifuging, selectively removing material of the pellet phase from the container. The selectively removing may include inserting an aspiration tube from outside of to inside of the container to contact the pellet phase inside the container and aspirating at least a majority of material of the pellet phase through the aspiration tube to outside of the container without suspending material of the pellet phase in a suspension liquid. Aspirating the material of the pellet phase without first suspending the material in a suspension liquid is sometimes referred to herein as direct aspiration of the material of the pellet phase. Such direct aspiration may be performed without removal of lower-density material phases from above the pellet phase, may be performed after removing some but not all of the lower-density material phases or may be performed after removing all of the lower-density material phases. The lower-density material phases may include an aqueous phase above the pellet phase and prior to the aspirating the lower-density aqueous phase may be not removed from above the pellet phase. Such aqueous phase may be left substantially in-tact within the container during the aspirating, and may remain in the container following the aspirating. Some or all of the lower-density material phases may remain in the container after the aspirating. The inserting may comprise inserting the aspiration tube downward into the container from above. When lower-density material phases remain in the container during the aspirating, the aspiration tube may be inserted downwardly through the lower-density material phases and into the material of the pellet phase located below the lower-density material phases. The aspiration tube may be a needle (e.g., hypodermic needle), cannula or other device with a fluid communication channel. For many applications, a 18 to 22 gauge hypodermic needle may be used for the aspiration tube. During the aspirating, the aspiration tube may be in fluid communication with a fluid receptacle, and the aspirating may include collecting at least a majority of the material of the pellet phase in the fluid receptacle. Such a fluid receptacle may be a syringe or other fluid containment apparatus. By selectively removing the material of the pellet phase without requiring prior removal of less-dense material phases above the pellet phase, the process operation of removing the pellet phase material may be considerably simplified and the potential for processing errors and for loss of cells to adhesion to apparatus surfaces may be significantly reduced. The fluid receptacle may be pre-loaded with a dispersion medium that mixes with the material of the pellet phase in the fluid receptacle when the dispersion material is introduced into the fluid receptacle during the aspirating. The dispersion medium may be a liquid medium to disperse and suspend the cells of the pellet phase material. The dispersion medium may be a gel or gel-like material in which the cells of the pellet phase material may disperse and be retained. The dispersion medium may be a delivery vehicle for the cellular material (e.g., leuko stromal vascular cells) of the pellet phase, and such cellular material may be administered to a patient in a delivery composition including the cellular material and the dispersion medium. Some examples for a dispersion medium that may be preloaded into the fluid receptacle include compositions that may be or include one or more of the following, either alone or with other components: saline solution (e.g., a balanced saline solution, Hank's Balanced Solution), crystalloid solution (e.g., Lactated Ringer's solution), hyaluronic acid and hyaluronic acid-based materials. Such hyaluronic acid-based materials may be substrate or carrier compositions based on hyaluronic acid. Any of these listed materials for possible use as or inclusion in a dispersion medium may also be part of a final delivery composition for administration to a patient. The volume of dispersion medium pre-loaded into the fluid receptacle may be any convenient volume for the application. In some preferred implementations, the dispersion medium may be present in a sufficient volume to prevent clumping of material of the pellet phase in the fluid receptacle. The dispersion medium in the fluid receptacle may have a volume such that a volume ratio of the volume of the dispersion medium to the volume of the pellet phase material introduced into the fluid receptacle during the aspirating is at least 1:1, at least 2:1, or at least 3:1. Often, such a volume ratio may be up to 10:1, up to 7:1, up to 5:1; up to 3:1 or up to 2:1. In some implementations, the dispersion medium in the fluid receptacle may have a volume of at least 1 milliliter, at least 2 milliliters or at least 3 milliliters. In some implementations, the dispersion medium in the fluid receptacle may have a volume of up to 10 milliliters, up to 7 milliliters, up to 5 milliliters, up to 3 milliliters or up to 2 milliliters. A mixture formed in the fluid receptacle during the aspirating may be further processed to prepare a delivery composition including material of the pellet phase or the mixture may be in the form of a delivery composition that is ready as prepared in the fluid receptacle for direct administration to a patient, such as by direct injection from the fluid receptacle into the patient following completion of the aspirating. Further processing may include centrifuging the mixture formed in the fluid receptacle to reform a pellet phase, separation of the pellet phase material from other, typically less-dense material phases, that form during the centrifuging, followed by formulation of the pellet phase with other components to prepare a desired delivery composition, which could include any of the components that could be used as the dispersion medium or any other components suitable for a delivery composition. When the delivery composition is to be injected into a joint, for example to treat osteoarthritis or a tissue defect, the delivery composition may in some preferred implementations have a total volume in a range having a lower limit of 0.5 milliliter, 1 milliliter or 2 milliliters and an upper limit of 5 milliliters, 4 milliliters or 3 milliliters. The delivery composition may include a volume of the pellet phase material in a range having a lower limit of 0.25 milliliter, 0.5 milliliter, 0.75 milliliter, or 1 milliliter and an upper limit of 2.5 milliliters, 2 milliliters or 1.5 milliliters. When the pellet phase material includes a concentrate of leuko stromal vascular cells, the delivery composition will include a mixture of the different cells present in the leuko stromal vascular fraction, without purification and without culturing. This is distinguishable from other treatment compositions that may be prepared using only certain types of cells separated from the leuko stromal vascular fraction mixture or using cultured cells.

In some implementations, selective removal of material of the pellet phase may involve removing one or more, or all, of the lower-density material phases layers from the container prior to removing material of the pellet phase from the container. One or more of the lower-density material phases may be removed from the container apparatus while retaining the pellet phase within the container apparatus. The lower-density material phases may be removed from the portable container apparatus in sequence of increasing density, which may include suctioning the lower-density material phases from the portable container apparatus through an open end of a suction conduit disposed in the portable container apparatus. Preferably, such an open end of a suction conduit may be disposed in the portable container apparatus not directly above the pellet phase, to reduce the possibility that suction created in the portable container apparatus would structurally disrupt the pellet phase. Removing the lower-density material phases may include progressively translating the suction conduit to lower elevations within the portable container apparatus as more of the lower-density material phases are removed from the portable container apparatus. In some preferred implementations, the pellet phase remains in place and stationary, relative to the portable container apparatus, while the lower-density material phases are removed. During the centrifuging, the pellet phase may form at a location within the portable container apparatus adjacent a bottom of the internal containment volume, and the pellet phase may remain at that location during the removing the lower-density material phases. In some implementations, removing the lower-density material phases may include tipping the portable container apparatus during suctioning of the lower-density material phases to promote flow of at least a final suction portion of the lower-density material phases within the portable container apparatus laterally away from the pellet phase and toward the open end of the suction conduit. The portable container apparatus may include a corner located lateral to the pellet phase, and which may be located at an elevation of the portable container apparatus that is higher than the bottom elevation of the pellet phase, or even higher than a top elevation of the pellet phase. The tipping may promote flow of fluid of the lower-density material phases laterally toward the corner for suctioning from the vicinity of the corner into the open end of the suction conduit. In some preferred implementations, the lower-density material phases are removed through a top of the portable container apparatus.

When lower-density material phases are removed from the container prior to removal of material of the pellet phase, the processing may include introducing aqueous suspension liquid into the portable container apparatus and dispersing cells of the pellet phase in the suspension liquid, such as to form a dispersion of the cells in the suspension liquid. The suspension liquid may be introduced into the portable container apparatus after the lower-density material phases have been removed. The suspension liquid may be introduced at a volume in a range having a lower limit of 0.25 milliliters and an upper limit of 40 milliliters. After being dispersed in a suspension liquid, the suspension liquid with dispersed cells may be removed from the container. Preferably at least most of the suspension liquid is removed from the container and more preferably substantially all of the suspension liquid and substantially all of the cells from the pellet phase are removed from the portable container apparatus with the suspension liquid. During centrifuging to prepare the pellet phase, the pellet phase may form within the portable container apparatus adjacent a bottom of the internal containment volume where the suspension liquid may mix with the pellet phase at that location to form the suspension. The suspension liquid and dispersed cells may be removed through a top of the portable container apparatus. The suspension liquid and dispersed cells may be removed upward through a hollow member disposed downward into the portable container apparatus, for example through a hollow needle or cannula, and may be drawn into a syringe in fluid communication with the hollow member. In some implementations, such a hollow member may pierce and extend across the filter. Such a hollow member may be an aspiration tube, as described above, and may be in fluid communication with a fluid receptacle, as described above.

The processing may include removing stromal vascular fraction cells of the pellet phase from the portable container apparatus, which may include the use of a suspension liquid as noted above. At least a majority of the stromal vascular fraction cells of the pellet phase may be removed from the portable container apparatus, and preferably all or almost all of the leuko stromal vascular cells of the pellet phase are removed from the portable container apparatus. After removing stromal vascular fraction cells from the portable container apparatus the method may include preparing a medical treatment composition for administration to a human, comprising mixing with a biocompatible scaffold material at least a portion, and preferably at least a majority, of the stromal vascular fraction cells removed from the portable container apparatus.

The digestion medium may provide collagen digestion units (CDU) per milliliter of catalytic volume that is within a range having a lower limit of 100, 150, 175 or 200 CDU and an upper limit of 400, 300, 275, 250 or 200 CDU, provided that the upper limit is larger than the lower limit. In some implementations, the digestion medium may provide about 200 CDU per millimeter of catalytic volume. In this regard, the catalytic volume is the total volume of the digestion medium added to the container and the volume of cancellous bone material already disposed within the container when the digestion medium is added. For example, if the volume of digestion medium added to the container equals the volume of cancellous bone material already disposed within the container, then the digestion medium will need to contain a concentration of collagenase enzyme that is twice as large as the desired concentration relative to the catalytic volume. As will be appreciated, the cancellous bone material as collected will include non-bone material, but in some preferred applications with thorough washing, the cancellous bone material should be cleaned of much of the non-bone material which may pass to and be removed from the filtrate side of the filter, while much of the cancellous bone of the cancellous bone material remains on the retentate side of the filter.

The digesting may include adding the digestion medium to the container such that the volume of the digestion medium is greater than the volume of the cancellous bone material within the portable container apparatus. The digestion medium may be added to the container at a volume ratio of the volume of digestion medium to volume of the cancellous bone material within the container is in a range of from 0.5:1 to 50:1.

The digesting may include permitting enzymatic digestion within the container apparatus for a retention time while the apparatus is in a temperature controlled environment, with the retention time being in a range having a lower limit of 15 minutes, 20 minutes, 25 minutes or 30 minutes and an upper limit of 60 minutes, 50 minutes, 45 minutes or 40 minutes. For various implementations, the retention time may be about 35 minutes.

The digesting may include at least occasional agitation of contents within the container during such retention time. The agitation may include some portion or substantially all of such retention time. The agitation may include mixing, periodically or continuously, with a rotatable mixer disposed within the portable container apparatus. The agitation may include periodic or continuous movement of the container to cause agitation of contents within the container. The agitation may include shaking the container, such as on a warmer-shaker. The agitation may be continuous and lasting during at least a majority of the retention time.

Temperature control may be implemented at various points in the processing of the method. The digestion medium when added to the portable container apparatus may be within a temperature range having a lower limit 32° C., 33° C., 34° C. or 35° C. and an upper limit of 38° C. or 37° C. The temperature within a temperature controlled environment during all or a portion of an above-noted retention time may be maintained in a temperature range having a lower limit of 32° C., 33° C., 34° C. or 35° C. and an upper limit of 38° C. or 37° C. The wash liquid, when added to the container, may be within a temperature range having a lower limit of 32° C., 33° C., 34° C. or 35° C. and an upper limit of 38° C. or 37° C.

The temperature controlled environment may be a warmer-shaker that provides the temperature controlled environment and provides a shaking agitation motion to the portable container apparatus.

The washing may include at least one wash cycle, and may include only a single wash cycle or may include multiple wash cycles (at least two wash cycles). Each wash cycle may comprise adding a volume of aqueous wash liquid to the container apparatus to contact the cancellous bone material within the container apparatus and removing at least a majority of the wash liquid with at least some non-bone constituents from the portable container apparatus from the filtrate volume and retaining at least a portion of the cancellous bone material containing stromal vascular fraction cells in the portable container apparatus disposed in the retentate volume. Such a wash cycle may include mixing the wash liquid and cancellous bone material in the portable container apparatus, at least for some time between adding and removing the wash liquid. For each wash cycle, it is preferred that at least a majority of the calcified bone component of the cancellous bone material is retained on the retentate side of the filter (in the retentate volume), along with a majority of the stromal vascular fraction cells contained in the cancellous bone material prior to the washing cycle. For each wash cycle, the volume of wash liquid addition may be controlled.

The washing may include at least one, at least two or more than two wash cycles. In some implementations, the washing may comprise at least three wash cycles. For many implementations, one wash cycle may be sufficient, while for other implementations, two or more wash cycles may be preferred.

Each wash cycle may comprise removing wash liquid (preferably at least a majority of the wash liquid and more preferably substantially all of the wash liquid) by suctioning from the container on the filtrate side of the filter (in the filtrate volume). During such suctioning, the wash liquid may be removed through a top of the portable container apparatus.

Mixing the wash liquid may include operating a rotatable mixer disposed in the portable container apparatus. The rotatable mixer may be manually operable, such as by a handle attached to a rotating shaft disposed through a top of the portable container apparatus. The mixing may include manually (hand) manipulating such a handle to manually rotate the mixer within the portable container apparatus. In various preferred implementations, such mixing may be performed following addition of the wash liquid, and preferably shortly following such addition, to thoroughly mix the wash liquid and the cancellous bone material being washed. Such a rotatable mixer may also be used to mix the digestion medium and the cancellous bone material following addition of the digestion medium to the container, and preferably shortly after such addition, to thoroughly mix the digestion medium and washed cancellous bone material to be digested.

The wash liquid used during the washing may but need not be of the same composition for each wash cycle. The wash liquid may include one or more additives. For example the wash liquid for one of more of the wash cycles may include one or more than one of an anti-clotting agent, an antibiotic and an antifungal. In some preferred implementations, for at least one wash cycle, the wash liquid includes at least one of an anti-clotting agent, an antibiotic or an antifungal. In other implementations, for at least one wash cycle, the wash liquid includes an anti-clotting agent, an antibiotic and an antifungal. One preferred example for an anti-clotting agent is heparin.

The processing of the method may include adding a stopping reagent to the portable container apparatus to stop enzymatic activity of the digestion medium within the portable container apparatus. The adding of a stopping reagent to the container may be performed for example, adding a stopping reagent not later than 60 minutes following adding the digestion medium to the container apparatus, not later than 50 minutes following such adding of the volume of digestion medium, not later than 45 minutes following such adding the volume of digestion medium, not more than 40 minutes following such adding the volume of digestion medium or not more than 35 minutes following such adding of the volume of digestion medium. The stopping reagent may comprise human albumin. The stopping reagent may be added in an amount sufficient to substantially stop enzymatic activity within the container. The stopping reagent may preferably be added before the centrifuging of the container following the digesting. The portable container apparatus may be configured to be disposed in a centrifuge to permit the apparatus to be centrifuged during the centrifuging. The portable container apparatus may be configured to be disposed in a standard-size centrifuge receptacle, or bucket. The processing may include after the washing and prior to the centrifuging, disposing the portable container apparatus in a centrifuge, and may include after the centrifuging, removing the portable container apparatus from the centrifuge.

The portable container apparatus may be conveniently transported between different locations for performance of different processing at the different locations, and preferably may be manually transported by being carried by a person. For example, a temperature controlled environment may be located at one location and the centrifuge may be located at a different location, and the method may comprise after the retention time in a temperature controlled environment, transporting the portable container apparatus from that location to the location of the centrifuge for performance of the centrifuging. As another example, one or more wash cycles may occur at yet a different location, and the method may comprise transporting the portable container apparatus from the location of a wash cycle to the location of the temperature controlled environment. By transporting the portable container apparatus from one location to another it is meant that the portable container apparatus, along with contents of the portable container apparatus, is physically moved from one location to the other location, whether or not there are intermediate stops along the way.

The portable container apparatus may have an access orientation, which may be a free-standing orientation. When the container is in the access orientation, all access into the portable container apparatus may in various implementations be through one or more ports extending through the top (e.g., through a lid) of the portable container apparatus and accessible from above the top of the portable container apparatus. Having all access into the portable container apparatus from above facilitates convenient addition and removal of materials from the portable container apparatus, without requiring special suspension or retention of the portable container apparatus and without requiring access from the side that may be more susceptible to moving or tipping the portable container apparatus. When in the access orientation, the portable container apparatus may be supported by a base that maintains the portable container apparatus in a stable, free-standing condition.

The portable container apparatus may include volume gradation markings on an exterior side, with the gradation markings indicating the quantity of volume occupied by a retentate volume within the portable container apparatus up to different elevations within the portable container apparatus, such as when the portable container apparatus is positioned in the access orientation. The gradation markings permit direct visual measurement of the quantity of the volume of material (e.g., cancellous bone material) disposed within the retentate volume. This makes it convenient for someone using the container to quickly identify the volume of material disposed within the retentate volume, and to quickly determine quantities of wash liquid or digestion medium to be added for washing or digesting operations. When the portable container apparatus includes such gradation markings, the wall with the gradation markings preferably has sufficient transparency to permit visual observation of the level of material disposed within the portable container apparatus.

The method permits convenient and controlled processing of various quantities of cancellous bone material in a convenient manner. The volume of cancellous bone material (including contaminants), disposed in the container on the retentate side of the filter (e.g., within a retentate volume) at commencement of the washing may often be in a range having a lower limit of 0.25 cubic centimeters and an upper limit of 100 cubic centimeters.

It should be appreciated that when reference is made to "cancellous bone material" or a volume thereof in relation to a method of the disclosure the reference may be to cancellous bone and associated non-bone material as removed from a patient or as initially disposed in the portable container apparatus, or to any portion or component of such material that is present in the portable container apparatus at any time during processing. Non-bone material in the cancellous bone material may be from biological materials extracted from subjects along with cancellous bone. Non-bone material that may be associated with cancellous bone may include for example bone marrow, blood, and other blood-derived tissues and fluids that may have been collected with cancellous bone or that result from degradation during tissue collection or during processing operations. The amounts of these non-bone components will generally be higher in unwashed cancellous bone material at the commencement of washing operations and will generally be lower at the commencement of digesting operations, following the washing. Immediately prior to the washing, the cancellous bone material within the retentate volume may comprise non-bone material including bone marrow and other blood-derived tissues and fluids. During the washing, at least a majority, and preferably all or almost all, of the bone marrow and other blood-derived tissues and fluids may be washed from the cancellous bone material and removed from the filtrate volume. At least a majority, and preferably all or almost all, of the calcified bone component of the cancellous bone material may be retained in the retentate volume throughout the washing. In some implementations, at least a majority, and preferably all or almost all, of the calcified bone component of the cancellous bone material may be retained in the retentate volume throughout the washing, digesting and centrifuging.

The portable container apparatus may be orientable in an access orientation for introducing material into the portable container apparatus. For convenience of description except as noted, the portable container apparatus is described as oriented in the access orientation. As such, relational references such as to top, bottom, up, down, above, below, elevations, vertical, horizontal and the like are in relation to the portable container apparatus as oriented in the access orientation. The portable container apparatus may be configured such that the portable container apparatus may be stably supported in the access orientation. For example, the portable container apparatus may have a base configured for interfacing with a flat, substantially horizontal surface (e.g., counter top or table top) to stably support the portable container apparatus in the access orientation, or may be held in a mounting structure that maintains the portable container apparatus in the access orientation. The portable container apparatus may be advantageously configured to permit performance of many different operations with the portable container apparatus when the portable container apparatus is oriented in the access orientation.

The portable container apparatus has a design that accommodates retention of the leuko stromal vascular cells in a single container during processing from introduction of cancellous bone material into the container through preparation of a concentrate product containing the target stromal vascular fraction cells.

In some preferred implementations, the filter may have a separation size in a range of from 70 microns to 800 microns. The filtrate volume may include a collection volume (i.e., a collection volume that is a part of the filtrate volume) and the collection volume may have a bottom elevation corresponding to a bottom elevation of the filtrate volume and a top elevation that is lower than the bottom elevation of the retentate volume. The portable container apparatus may include an inlet port in fluid communication with the retentate volume and configured for introducing cancellous bone material directly into the retentate volume. The portable container apparatus may include a suction port that is in fluid communication with the filtrate volume and provides access to the filtrate volume for suctioning from the filtrate volume material that may pass through the filter from the retentate volume to the filtrate volume, for example biological fluids and small particles that may separate from cancellous bone material introduced into the retentate volume.

The retentate volume and the filtrate volume of the portable container apparatus may be separated by the filter. By being "separated" by the filter it is meant that the filter forms at least a portion of the defining physical separation between the retentate volume and the filtrate volume. As will be appreciated, the filter accommodates movement of fluid and undersize non-fluid material (e.g., liberated undersize cells, tissue fragments, etc.) between the retentate volume and the filtrate volume, while retaining oversize material within the retentate volume. As discussed elsewhere herein, the portable container apparatus may be configured to be received in a centrifuge for centrifuging the portable container apparatus, and such centrifuging may assist to concentrate the target stromal vascular fraction cells in the collection volume.

The portable container apparatus may be used during multiple processing steps to prepare a stromal vascular fraction concentrate (e.g., concentrate rich in stromal vascular fraction cells) from cancellous bone material without the need to transfer the material being processed between different containers for different processing steps. The portable container apparatus may be used initially to collect the cancellous bone material during a surgical operation as the cancellous bone is being removed during the surgical operation, or the cancellous bone material may be introduced into the portable container apparatus at some time following initial collection. The portable container apparatus may be easily transportable between locations where collection or different processing operations may be conducted.

The portable container apparatus may include an extraction port in fluid communication with the internal containment volume and configured for removing processed biological material from the internal containment volume. Any or all of the inlet port, the suction port and the extraction port may be configured for access therethrough from above the portable container apparatus into the internal containment volume. The extraction port may be located above a portion of the filter, so that the advancing tip of a hypodermic needle pierces the filter when the tip of the hypodermic needle is advanced from the extraction port into the collection volume. The collection volume may include a nadir and the extraction port may be positioned above the nadir so that the tip of a hypodermic needle inserted through the extraction port may be advanced vertically downward to the vicinity of the nadir of the collection volume.

The portable container apparatus may include a mixing device disposed at least in part within the retentate volume for mixing contents within the retentate volume. The mixing device may comprise a rotatable shaft extending from outside of the internal containment volume to inside of the internal containment volume. The shaft may be made of a polymeric or metallic material of construction. A preferred material of construction for the shaft is stainless steel, for example 303, 304 or 316 stainless steel. If a polymeric material of construction is used, it should preferably be high-strength, for example an Ultem™ resin composition available from Saudi Basic Industries Corp. (SABIC). The shaft may comprise at the top a tapered receptacle adapted to mate with a tapered syringe tip. The tapered receptacle may be fitted with an o-ring to seal against the tapered syringe tip when inserted into the tapered receptacle, thereby permitting a good suction to be applied by the syringe through the lumen to extract material from the retentate volume. The shaft may comprise a handle interface outside of the internal containment volume. The portable container apparatus may further include a handle interfaced to the handle interface, wherein rotating the handle causes the shaft to rotate, thereby operating the mixing device. The handle may be removably interfaced to the handle interface, to permit the handle to conveniently be connected with the handle interface to operate the mixing device when appropriate and to conveniently be removed from the handle interface to permit access to a top of the portable container apparatus without interference from the handle. The portable container apparatus may include a lumen that extends through the shaft and has a proximal end located outside of the internal containment volume and a distal end located within the internal containment volume. Such a lumen may provide access from outside of the internal containment volume to inside of the internal containment volume. A removable plug for sealing the lumen may be disposed in the proximal end of the lumen. The shaft may be rotatable about an axis that extends through the collection volume. The lumen may be aligned with the axis. The lumen may provide access to the collection volume for aspiration of material therefrom and/or injection of material thereto.

The portable container apparatus may be configured for advancing a hypodermic needle through a lumen and out of the distal end of the lumen to access the collection volume with an advancing tip of the hypodermic needle. The distal end of the lumen may be located in the retentate volume above a portion of the filter, so that the advancing tip of the hypodermic needle may pierce and pass through the filter when the tip of the hypodermic needle exits the distal end of the lumen and is advanced from the distal end of the lumen into the collection volume. The collection volume may include a nadir, and an axis of the lumen may be aligned so that the tip of a hypodermic needle exiting the distal end of the lumen may be advanced to the vicinity of the nadir of the collection volume. The hypodermic needle may thus access the collection volume to permit injection of material into and/or aspiration of material from the collection volume (e.g., aspiration of stromal vascular fraction concentrate from the collection volume). The portable container apparatus may be designed for single-use, and piercing the filter with a hypodermic needle may beneficially provide a safety mechanism for preventing reuse, and risks associated therewith, by damaging the filter in a way that renders the filter unsatisfactory for reuse.

The mixing device, or mixer, may comprise one or more mixing members disposed in the retentate volume and connected with the shaft, wherein the mixing member moves through the retentate volume when the shaft is rotated. For example, a mixing member may be in the form of impeller blades, paddles or arms that agitate and mix components within the retentate volume when the shaft is rotated. At least a portion of the retentate volume may be within a tapered portion of the internal containment volume (with at least a portion of the tapered portion being located above a bottom elevation of the retentate volume), and at least a portion of one or more such mixing member may be disposed within the tapered portion of the internal containment volume. The mixing device may include a filter contact member that moves when the shaft is rotated and movably contacts the filter. The filter contact member may be part of or separate from such a mixing member. The filter contact member contacts the filter at least periodically, and may contact the filter continuously when the shaft is rotated. The filter contact member may advantageously deform the filter when it moveably contacts the filter, promoting dislodgment of material from the filter to help prevent filter clogging.

As noted, the portable container apparatus may include a suction port in fluid communication with the filtrate volume. By the suction port being in fluid communication with the filtrate volume, it is meant that the suction port is fluidly connected directly to the filtrate volume, and not indirectly through the retentate volume and the filter. The fluid communication may be provided by a dedicated conduit extending from the suction port to a desired location within the filtrate volume where it is desired to apply suction directly to the filtrate volume. The suction port may be in fluid communication with a tapered portion of the internal containment volume through a conduit providing fluid communication from the suction port to a location within the filtrate volume that is also within the tapered portion of the internal containment volume. The conduit may extend through the filtrate volume from adjacent the suction port to such a location within the filtrate volume. The suction port may be located above a tapered portion of the internal containment volume. The suction port may be configured for access through the suction port from above the portable container apparatus. The suction port may be configured for connection to a vacuum system to suction material from the filtrate volume, such as material that passes through the filter from the retentate volume to the filtrate volume.

The portable container apparatus may include multiple suction ports. For example, the portable container apparatus may include a first suction port as described in the preceding paragraph that is in fluid communication with a first location in the filtrate volume within a tapered portion of the internal containment volume through a first conduit, and the portable container apparatus may include a second suction port through which components passing through the filter from the retentate volume to the filtrate volume may be suctioned from the filtrate volume through a second conduit extending from the second suction port to a second location within the filtrate volume. The second conduit may be configured to permit adjustment of the elevation of the second location within the filtrate volume. The second conduit may be translatable through the second suction port to adjust the elevation of the second location within the filtrate volume. The second conduit may be configured so that at any extent of such adjustment of the second location, the second location will always be at a higher elevation within the filtrate volume than the first location, which may be fixed. The second conduit may be configured to permit adjustment of the position of the second location within the filtrate volume at different elevations above a tapered portion of the filtrate volume. The second conduit may be configured to permit positioning the second location at an elevation corresponding with an interface between a tapered portion of the filtrate volume and a portion of the filtrate volume located above the tapered portion, which may be the lowest elevation to which adjustment is permitted. The second suction port may be configured for access through the second suction port from above the portable container apparatus.

Any one or more of an inlet port, suction port of other ports providing access to the internal containment volume may be configured for access through the port from above. In this way, access through each such port may be conveniently from above the portable container apparatus, providing a significant advantage to a user of the portable container apparatus in that such a user may focus all access manipulations from above the portable container apparatus while the portable container apparatus is in a normal position in the access orientation, for example with the portable container apparatus freestanding on a flat work surface such as a table or counter. Complexities associated with access from the side or from below may be avoided, including the complexity of sealing and providing access into side or bottom access ports against a positive fluid head that may be present in the portable container apparatus and the complexity of awkward side or bottom interactions by users. Although such access from above the portable container apparatus may be at some angle relative to vertical, in a preferred implementation the access through such port is in a vertical direction from above the portable container apparatus. In one preferred implementation, all access to the internal containment volume may be through access ports wherein each such access port (e.g., inlet port, suction port, extraction port, other ports) is configured for access through the access port only from above the portable container apparatus. In another preferred implementation, all access ports may be configured for access through each such access port in a vertical direction from above the portable container apparatus.

The internal containment volume of the container may have a tapered portion that tapers in a downward direction. Such a tapered portion of the internal containment volume may have a cross-sectional area that tapers, or reduces in size, in a direction toward the bottom of a collection volume. A tapered portion of the containment volume helps to direct and concentrate target dense material (e.g., stromal vascular fraction cells) toward and into the collection volume. At least a portion of the collection volume may be located within or below such a tapered portion. At least a part of the tapered portion may be located above the collection volume. The tapered portion of the internal containment volume may have a conical shape or any other shape with a cross-sectional area that tapers to reduce in size in a direction toward the bottom of the collection volume. In various implementations, at least a part of the tapered portion may be located above (at a higher elevation than) the collection volume. At least a portion of the tapered portion may be located below (at a lower elevation than) the bottom elevation of the retentate volume. The tapered portion may have a uniform taper geometry (e.g., constant rate of taper) or may have a varying taper geometry (e.g., varying rate of taper in the direction of the taper).

The portable container apparatus may comprise a fluid containment shell with an internal cavity portion forming at least a part of the internal containment volume. The internal cavity portion may be open to above. The portable container apparatus may include a lid attached to the shell and disposed to cover from above the internal cavity portion within the shell. One or more than one of the suction port the inlet port or other access port may pass through the lid. In one preferred implementation, all access into the internal containment volume may be only through one or more openings, or ports, passing through the lid. The filter may be suspended from the lid. The mixing device may be supported by the lid and extend vertically downward from the lid into the retentate volume. The portable container apparatus may include a flow barrier skirt, for example, that may extend between 5 mm and 50 mm downward from the lid into the internal containment volume. The shell may comprise walls around the internal cavity portion except where the cavity portion is open to above, and the portable container apparatus may be configured with no access into the internal containment volume through the walls of the shell. The shell may comprise an upper portion having a first wall surface portion defining a corresponding upper portion of the internal containment volume. Substantially all of the first wall surface portion may have a steep incline relative to horizontal, for example an incline of at least 65°, preferably an incline of at least 75° and more preferably an incline of about 90° (vertical wall surface). The shell may include a lower portion located below the upper portion and having a second wall surface portion defining a corresponding lower portion of the internal containment volume, and the second wall surface portion may include a tapered wall surface portion defining the tapered portion of the internal containment volume. The tapered wall surface portion may have a less steep incline relative to horizontal than the first wall portion of the upper portion. The angle of incline relative to horizontal of the tapered wall portion (taper angle), or of the entire second wall portion when comprised entirely of the tapered wall portion, may be in a range having an upper limit of 70°, 65°, 60°, 55°, 50 or 48 and a lower limit of 20°, 25°, 30°, 35°, 40°, 42° or 45°, with one preferred range being from 40° to 50° and another preferred range being 42° to 48°. The tapered portion of the internal containment volume may occupy substantially the entire lower portion of the internal containment volume, and the second surface may be made up entirely or substantially entirely by the tapered wall surface. At least a first portion of the filter may be disposed in the upper portion of the internal containment volume and a second portion of the filter may be disposed in the lower portion of the internal containment volume. The incline of each of the first wall surface portion, the second wall surface portion and the tapered wall surface portion need not be uniform, however all portions of the first wall surface portion may preferably be at a steeper incline than the incline of any portion of the tapered wall surface portion.

There are a number of advantages that may be available with configurations of the preceding paragraph including an upper portion having a steeper wall surface incline and a lower portion having a less steep wall surface incline. Such a structure advantageously accommodates a larger proportion of the internal containment volume being allocated to the retentate volume, with a larger portion of the retentate volume in the upper portion of the shell and a smaller portion of the retentate volume in a lower portion of the shell. The tapered wall surface portion of the lower portion of the shell helps to direct fluid and other material in the filtrate volume toward the bottom of the filtrate volume for efficient collection and removal. The tapered wall surface also directs material toward the collection volume, which may generally be located in a bottom portion of the filtrate volume. The portable container apparatus may also be configured to be centrifugable, and centrifuging will tend to accelerate concentration of a most dense fraction (e.g., stromal vascular fraction) in the collection volume.

A tapered portion of the internal containment volume may have a tapered portion nadir corresponding with a bottom elevation of the internal containment volume. The bottom elevation of a collection volume may correspond with the bottom elevation of the internal containment volume. Wall surfaces of the portable container apparatus defining a tapered portion of the internal containment volume may coverage at a point at the tapered portion nadir. This is a particularly beneficial configuration, especially for applications when target material is to be collected in and removed from the collection volume in the vicinity of the tapered portion nadir.

In some implementations, the internal containment volume may have at least a first tapered portion and a second tapered portion that is located vertically lower than the first tapered portion, wherein the first tapered portion has a greater rate of taper than the second tapered portion. The first tapered portion may be defined at least in part by a first internal wall surface of the container that is at a first angle relative to horizontal when the apparatus is in an access orientation in a range for the tapered portion discussed above. The second tapered portion may be defined at least in part by a second internal wall surface of the container that is at a second angle relative to horizontal when the apparatus is in an access orientation in a range having a lower limit of 50°, 60°, 65° or 70° and an upper limit of 89°, 88°, 85° or 82°, provided that the second angle is larger than the first angle. Such a first tapered portion, for example as viewed in a vertical plane cross-section, may be defined at least in part by opposing ones of such first internal wall surfaces. Such a second tapered portion in such a vertical cross-section may be defined at least in part by opposing ones of such second internal wall surfaces. The second tapered portion may be disposed partially or entirely within the filtrate volume. The second tapered portion may include at least a portion of a collection volume within the filtrate volume or may be entirely within such a collection volume. The second tapered portion may be or may be a part of a pellet well located in a bottom portion of such a collection volume. The volume within the second tapered portion of the internal containment volume may be in a range having a lower limit of from 0.2 percent, 0.3 percent, 0.5 percent, 0.7 percent or 0.8 percent of the portion of available processing volume of the container that is within the tissue retention volume and an upper limit of 2.5 percent, 2 percent, 1.5 percent, 1.2 percent or 1.1 percent of the portion of such available processing volume of the container that is within the tissue retention volume. Such a portion of the available processing volume within the tissue retention volume may be a volume capacity of the apparatus for human biological material feed (e.g., cancellous bone material) that may be processed in the apparatus. For some implementations, the second tapered portion of the internal containment volume may have a volume in a range having a lower limit of 0.3 cubic centimeter, 0.5 cubic centimeter, 0.7 cubic centimeter, 0.8 cubic centimeter, 0.9 cubic centimeter or 1.0 cubic centimeter and an upper limit of 5 cubic centimeters, 3 cubic centimeters, 2 cubic centimeters, 1.5 cubic centimeters, or 1.3 cubic centimeters. The second tapered portion may have a vertical dimension when the apparatus is in an access orientation of at least 0.5 centimeter, at least 1 centimeter, at least 1.5 centimeters, at least 2 centimeters or at least 2.5 centimeters. The second tapered portion may have a vertical height dimension when the apparatus is in an access orientation of up to 10 centimeters, up to 5 centimeters, up to 4 centimeters or up to 3 centimeters. The internal containment volume may include a third tapered portion that is located below the second tapered portion that has a greater rate of taper than the second tapered portion. A third tapered portion may be defined at least in part by a third internal wall surface of the container that is at an angle relative to horizontal that is smaller than the second angle. The third angle may have a value as described previously for the first angle, provided that the second angle is larger than the third angle. The third tapered portion may occupy the lowermost portion of a collection volume in the filtrate volume, which may be a lowermost portion in a pellet well. The third tapered portion may have a vertical height dimension when the apparatus is in an access orientation that is smaller than a vertical height dimension of the second tapered portion. The third tapered portion may have such a vertical height dimension that is no larger than 1 centimeter, no larger than 0.5 centimeter, or no larger than 0.3 centimeter. The third tapered portion may have a volume that is smaller than the volume of the second tapered portion. The third tapered portion may have a volume that is no larger than 0.5 cubic centimeter, no larger than 0.3 cubic centimeter or no larger than 0.2 cubic centimeter. The first tapered portion may have a vertical height dimension below a bottom of the filter that is smaller than a vertical height dimension of the second tapered portion, and such a vertical height dimension of the first tapered portion may be at least 0.5 centimeter or at least 1 centimeter. The first tapered portion may beneficially help stromal vascular fraction materials to move into the second tapered portion when the apparatus is centrifuged. The second tapered portion, and also the third tapered portion if present, may be or be part of a pellet well, as discussed below.

Material of a pellet phase containing a concentrate of leuko stromal vascular cells, such as may be formed during centrifuging, may be directly aspirated from a collection volume at the bottom of the filtrate volume without first removing overlying less-dense material phases and without dispersing the material of the pellet phase in a suspension liquid. Although the pellet phase may typically have a very high viscosity, it has been found that it is possible to aspirate the pellet phase material, for example though a hypodermic needle, without first diluting the pellet phase material to reduce viscosity, and without detrimental breakthrough of overlying, low viscosity aqueous liquid phase during the aspiration. This permits significant simplification in processing to remove such pellet phase material in some implementations.

The internal containment volume of the apparatus of the first aspect may include a pellet well that may help facilitate effective removal of pellet phase material by direct aspiration. The pellet well may be disposed in a bottom portion of the filtrate volume below a bottom elevation of the filter and accessible only from above when the apparatus is in an access orientation. Such a pellet well that may be configured as a relatively deep, narrow chamber to help facilitate effective direct aspiration of pellet phase material, such as a concentrate of leuko stromal vascular cells.

A pellet well may include a second tapered portion, and also optionally a third tapered portion, of the internal containment volume below a first tapered portion, as described above.

The filtrate volume may include a lower tapered portion below a bottom elevation of the filter and above a top elevation of a pellet well. The lower tapered portion of the filtrate volume may be defined by internal wall surfaces of the container that are each inclined relative to horizontal at a maximum angle of no larger than 60° when the container is in an access orientation. The lower tapered portion of the filtrate volume may be or include that portion of a first tapered portion of the internal containment volume, as discussed above, that is located below the filter. At least a portion of the pellet well may be defined by a wall surface of the container inclined relative to horizontal at an angle that is larger than the maximum angle when the apparatus is in the access orientation. The wall surface of the container defining at least a portion of the pellet well may be inclined relative to horizontal at an angle of at least 70°, at least 75°, at least 80°, or at least 85°. The wall surface of the container defining at least a portion of the pellet well may be inclined relative to horizontal at an angle of 90° (vertical) or less than 90°, when the apparatus is in the access orientation.

A pellet well may have a volume in a range having a lower limit of 0.3 cubic centimeter, 0.5 cubic centimeter, 0.7 cubic centimeter, 0.8 cubic centimeter, 0.9 cubic centimeter or 1.0 cubic centimeter and an upper limit of 5 cubic centimeters, 3 cubic centimeters, 2 cubic centimeters, 1.5 cubic centimeters, or 1.3 cubic centimeters.

A pellet well may have a vertical height dimension when the apparatus is in an access orientation of at least 0.5 centimeter, 1 centimeter, at least 1.5 centimeters, at least 2 centimeters or at least 2.5 centimeters. A pellet well may have a vertical height dimension when the apparatus is in an access orientation of up to 10 centimeters, up to 5 centimeters, up to 4 centimeters, up to 3 centimeters or up to 2 centimeters.

A pellet well may have at least one portion with a vertical length of at least 0.5 centimeter or at least 1 centimeter; a maximum horizontal cross-dimension across the pellet well in that vertical length portion of no larger than 10 millimeters, no larger than 8 millimeters or no larger than 5 millimeters; and a minimum horizontal cross-dimension in that vertical length portion of no smaller than 2 millimeters or no smaller than 1.5 millimeters. Having at least one such vertical length portion may facilitate receiving a distal end of a hypodermic needle or other aspiration tube in a relatively deep, narrow volume for aspiration of pellet phase material without significant premature breakthrough of less-dense aqueous liquid phase that may be disposed above the pellet phase following centrifuging. In some applications, such an aspiration tube (e.g., needle) may have an outer diameter of at least 1 millimeter. In some applications, the aspiration tube (e.g., needle) may have an outer diameter of no larger than 3 millimeters, no larger than 2.5 millimeters or no larger than 2 millimeters.

The portable container apparatus may be configured with a very convenient size from a number of perspectives, and with efficient use of the internal containment volume to facilitate processing of cancellous bone material to prepare and recover a concentrate with stromal vascular fraction cells. The portable container apparatus may be sized for convenient hand transportation, such as between a location where cancellous bone material is introduced into the container or some processing operation is performed and other, different locations, where some other processing operation may be performed. The portable container apparatus may also be sized for convenient manipulation by a person.

For many applications, the portable container apparatus may be sized and configured such that the internal containment volume has a volume in a range with a lower limit of 30 cubic centimeters, 50 cubic centimeters, 75 cubic centimeters, 100 cubic centimeters, 200 cubic centimeters, 300 cubic centimeters or 500 cubic centimeters and an upper limit of 1500 cubic centimeters, 1300 cubic centimeters, 1100 cubic centimeters, 1000 cubic centimeters, 900 cubic centimeters or 800 cubic centimeters, 700 cubic centimeters, 600 cubic centimeters, 500 cubic centimeters, 400 cubic centimeters or 300 cubic centimeters, provided that the upper limit is larger than the lower limit. One preferred range for many applications is for the internal containment volume to be in a range of 75 cubic centimeters to 500 cubic centimeters. By internal containment volume, it is meant the total internal volume contained within the walls defining the container portion of the portable container apparatus, including volume that is occupied by internal hardware, such as for example may be occupied by a mixing device, barrier member, suction conduits, barrier skirt, etc. As will be appreciated, less than all of the internal containment volume will be available for processing within the internal containment volume.

The terms "available processing volume", "useful volume" and "internal processing volume" are used interchangeably herein to refer to the portion of the internal containment volume that is effectively available to receive and process human biological material (e.g., cancellous bone material) and additives (e.g. wash solution, enzyme solution, other additives) during use of the portable container apparatus to process cancellous bone material. This available processing volume is equal to the internal containment volume less portions of the internal containment volume occupied by hardware (e.g., mixing device, filter, skirt, suction tubes, barrier member, etc) and less unoccupied portions of the internal containment volume not effectively accessible for occupation by biological material and additives during processing. For example, the available processing volume may exclude a small volume at the top of the container that is above a bottom extension of the inlet port into the internal containment volume. This small void space may be beneficial to permit space for fluid to slosh within the container when contents of the container may be internally mixed or externally agitated (e.g., by a shaker table). For many applications, the available processing volume may be in a range having a lower limit of 25 cubic centimeters, 50 cubic centimeters, 100 cubic centimeters, 75 cubic centimeters, 200 cubic centimeters, 300 cubic centimeters, 400 cubic centimeters and an upper limit of 1300 cubic centimeters, 1100 cubic centimeters, 1000 cubic centimeters, 900 cubic centimeters, 850 cubic centimeters, 800 cubic centimeters, 700 cubic centimeters, 600 cubic centimeters, 500 cubic centimeters, 400 cubic centimeters, 350 cubic centimeters, 300 cubic centimeters or 250 cubic centimeters, provided the upper limit is larger than the lower limit. In one preferred implementation for many applications, the available processing volume may be in a range of from 50 cubic centimeters to 400 cubic centimeters.

Advantageously, the portable container apparatus may be configured so that a large portion of the available processing volume is within the retentate volume, while still permitting a high level of performance for various processing operations. The retentate volume may comprise at least 55 percent, at least 60 percent, at least 65 percent or at least 70 percent of the available processing volume with the portable container apparatus. Often, the retentate volume will comprise not more than 95 percent, not more than 90 percent or not more than 85 percent of the available processing volume. For many preferred implementations, the retentate volume may comprise a portion of the available processing volume that is at least 10 cubic centimeters, at least 20 cubic centimeters, at least 40 cubic centimeters, at least 60 centimeters, at least 75 cubic centimeters, at least 100 cubic centimeters, at least 150 cubic centimeters or at least 200 cubic centimeters. The portable container apparatus may advantageously be configured with only a small portion of the available processing volume occupied by a collection volume, located below the filter. For example, the collection volume may comprise no more than 90 percent, no more than 10 percent, no more than 7 percent or no more than 5 percent of the available processing volume. The retentate volume may often be no larger than 400 cubic centimeters, no larger than 350 cubic centimeters, no larger than 300 cubic centimeters or no larger than 200 cubic centimeters.

For many preferred implementations a collection volume may be no larger than 50 cubic centimeters, no larger than 30 cubic centimeters, no larger than 20 cubic centimeters or no larger than 10 cubic centimeters. The collection volume may often be at least 0.5 cubic centimeter, at least 1 cubic centimeter, at least 2 cubic centimeters or at least 3 cubic centimeters. Typically, the entire collection volume will make up part of the available processing volume.

The portable container apparatus may be sized and configured to be containable within a relatively small envelope volume which may be particularly advantageous given the relatively large internal containment volume, available processing volume and retentate volume that may be provided in the portable container apparatus. For some preferred implementations, the portable container apparatus may be sized and configured to be containable within a first envelope volume defined by a rectangular cuboid having a length dimension of no more than 16 centimeters, a depth dimension of no more than 15 centimeters and a height dimension of no more than 18 centimeters. However, the portable container apparatus may be sized and configured to have some minimum size, for example as a function of a desired size of internal containment volume, available processing volume or retentate volume.

The filter may be of any appropriate filter media design. The filter may be any porous structure with openings sized to make a desired separation. The filter may be in the form of a mesh filter bag disposed within the internal containment volume, and that separates the internal containment volume between the retentate volume and the filtrate volume located on opposite sides of the filter bag. The filter may be a rigid mesh screen. In some implementations, the filter may have a separation size in a range having a lower limit of 70 microns, 100 microns, 150 microns, at 175 microns, 200 microns, 300 microns or 400 microns and an upper limit of 800 microns, 700 microns, 600 microns, 500 microns, 475 microns, 450 microns, 425 microns, 400 microns, 350 microns, 300 microns or 250 microns; provided that in the upper limit is larger than the lower limit. Stromal vascular fraction cells will pass through a 200 micron filter, however a somewhat larger filter size may be advantageous to promote recovery of most or substantially all of the leuko stromal vascular cells in the filtrate volume. Smaller size filters may plug to a degree that significantly reduces cell yield in terms of cell collection in and recovery from the filtrate volume. By separation size, it is meant the size at which the filter effects separation between particles passing through and particles rejected by the filter during normal operation. In one preferred implementation, the filter may be a mesh filter. The separation size may be determined by the size of openings provided in a surface filter, such as the mesh size of a mesh bag filter or of a rigid mesh screen filter.

The portable container apparatus may be configured to facilitate effective processing of a wide range of cancellous bone material feed volumes and that may be compatible with a large number of common centrifuges for some preferred applications. When in the access orientation, the internal containment volume may include a first portion that is cylindrical or is frustoconical tapering toward the bottom of the internal containment volume with an angle of taper relative to horizontal at a first angle; a second portion disposed below the first portion, the second portion being frustoconical tapering toward the bottom of the internal containment volume with an angle of taper relative to horizontal at a second angle; and a third portion disposed below the second portion in the pellet well, the third portion being cylindrical or frustoconical tapering toward the bottom of the internal containment volume at an angle of taper relative to horizontal at a third angle, with the first angle and the third angle being larger than the second angle. The first angle and the third angle may each independently be at least 70°, at least 75°, at least 80°, or at least 85°. The second angle may be in a range having a lower limit of 30°, 40°, 42° or 45° and an upper limit of 60°, 55°, 50°, 48° or 45°, provided the upper limit is higher than the lower limit. The second angle may be about 45°. The pellet well may be or have any features described elsewhere herein. Pellet well may be accessible to remove pellet phase material from the pellet well only from above. The filter may have a lower tapered portion that is disposed at least in part in the second portion of the internal containment volume above the pellet well. The portable container apparatus may have a mixing impeller with a tapered blade portion that corresponds with at least a portion of a tapered filter portion. The internal containment volume may be defined at least in part by a shell. The portable container apparatus may have some preferred dimensions in some implementations. The shell may have a cross-section, which may preferably be a circular cross-section, configured to fit within a centrifuge receptacle (e.g., centrifuge bucket) for centrifuging the portable container apparatus. The shell, a portion of the shell configured to be received in a centrifuge receptacle, the internal containment volume and/or a portion of the internal containment volume configured to be received in a centrifuge receptacle may have a maximum cross-section taken horizontally through the shell that may be fit entirely within a circle with a diameter not larger than 16 centimeters, not larger than 14 centimeters, not larger than 12 centimeters, not larger than 10 centimeters, not larger than 8 centimeters or not larger than 7 centimeters. Any such maximum cross-section may be such as to not fit entirely within a circle having a diameter of not smaller than 2 centimeters, not smaller than 3 centimeters, not smaller than 4 centimeters or not smaller than 6 centimeters. The shell, a portion of the shell configured to be received in a centrifuge receptacle, the internal containment volume and/or a portion of the internal containment volume configured to be received in a centrifuge receptacle may have a height dimension in a range having a lower limit of 2 centimeters, 3 centimeters, 4 centimeters, 5 centimeters or 6 centimeters and an upper limit of 16 centimeters, 14 centimeters, 12 centimeters, 10 centimeters, 8 centimeters or 7 centimeters. The portable container apparatus may have a total height in a range having a lower limit of 2 centimeters, 3 centimeters, 4 centimeters, 6 centimeters and 8 centimeters and an upper limit of 26 centimeters, 23 centimeters, 20 centimeters, 17 centimeters, 14 centimeters or 12 centimeters. The portable container apparatus may have an internal processing volume in a range of from 5 cubic centimeters, 10 cubic centimeters, 20 cubic centimeters, 50 cubic centimeters, 100 cubic centimeters, 150 cubic centimeters or 200 cubic centimeters and an upper limit of 400 cubic centimeters, 350 cubic centimeters, 300 cubic centimeters, or 200 cubic centimeters, with the upper limit being larger that the lower limit.

The filter may be of a flexible or a rigid mesh material. In a preferred implementation, the filter may be made of mesh material, more preferably a nylon mesh material. The filter need not be continuous, and may be comprised of discrete filter areas disposed at different locations between the retentate volume and the filtrate volume. Alternatively, the filter may be comprised of a single continuous filter area. The filter defines at least part of the physical separation between the retentate volume and the filtrate volume; it need not define all of the physical separation between the retentate volume and the filtrate volume. For example, there may be internal walls defining at least a part of the physical separation between the retentate volume and the filtrate volume, with an example being a skirt barrier that may be disposed at the top of the internal containment volume and that may define a separation between the retentate volume and the filtrate volume in an upper portion of the internal containment volume. As another example, the filter may include filter areas supported by a frame, with structural members of the frame defining a part of the physical separation between the retentate volume and the filtrate volume. In a preferred implementation, the portion of the physical separation between the retentate volume and the filtrate volume that is provided the filter should generally be large to provide as much filter surface area as reasonably possible.

The portable container apparatus may be configured to be received by a centrifuge for centrifuging. For example, the apparatus may be conveniently sized and configured to be received within a centrifuge bucket, and preferably of a commercially available centrifuge. Two or more of the portable container apparatus may be centrifuged simultaneously in a centrifuge. In one preferred implementation, the portable container apparatus may be sized and configured so that two of the portable container apparatus may be simultaneously centrifuged together in a dual bucket assembly, wherein each portable container apparatus counterbalances the other portable container apparatus during centrifuging, for efficient processing. Alternatively one portable container apparatus could be processed with a blank weight as a counterbalance. The portable container apparatus may be received in a centrifuge bucket with the bottom of the portable container apparatus adjacent to and facing the bottom of the bucket.

The portable container apparatus may include an extraction port in direct fluid communication with the filtrate volume and through which material is removable from the filtrate volume separate from the suction port. In a preferred implementation, access through the extraction port is in a vertical direction from above the portable container apparatus, for example with the extraction port passing through the top of the portable container apparatus.

The portable container apparatus may be configured for the addition of additives to the internal containment volume, and in particular directly into the retentate volume. As used herein, such an additive is any material added to the internal containment volume other than the cancellous bone material to be processed in the portable container apparatus. Such an additive may be added for example to aid processing within the portable container apparatus. Example of some additives to aid processing may include wash liquid, enzymes or surfactants. Such additives may be added to the retentate volume through an inlet port.

The portable container apparatus may, in addition to an inlet port, include a second port in fluid communication with the retentate volume for introducing an additive directly into the retentate volume. The second port, which may be referred to as an auxiliary port or as an additive port, may be conveniently sized and configured for insertion therethrough of a hypodermic needle from which an additive material may be ejected from the needle into the retentate volume or through which material may be removed from the retentate volume. This auxiliary port may be configured to make a luer connection with a syringe.

The portable container apparatus may include human biological material disposed in the internal containment volume, which human biological material may include cancellous bone material as originally introduced into the portable container apparatus or some processed portion of such initial cancellous bone material in a form as present at some stage during processing in the portable container apparatus. The portable container apparatus may include a concentrate with stromal vascular fraction cells disposed in a collection volume. Such a concentrate may be a pellet phase resulting from centrifuging.

A second aspect of the disclosure is provided by a medical product comprising a portable container apparatus having a filter disposed in an internal containment volume of the processing portable container apparatus and the internal containment volume includes a retentate volume on one side of the filter and a filtrate volume on another side of the filter. The portable container apparatus includes human biological material disposed in the internal containment volume, which human biological material includes cancellous bone material or some component or components derived from cancellous bone material.

A number of feature refinements and additional features are applicable to the second aspect of the disclosure. These feature refinements and additional features may be used individually or in any combination. As such, each of the following features may be, but are not required to be, used with any other feature or combination of the second aspect or other aspects of the disclosure.

The human biological material disposed in the internal containment volume may be cancellous bone material as initially introduced into the portable container apparatus or some processed portion of such cancellous bone material in a form as present at some stage during processing in the portable container apparatus, for example at some stage during processing according to the first aspect of the disclosure. The portable container apparatus may include a concentrate with stromal vascular fraction cells disposed in a collection volume. Such a concentrate may be a pellet phase resulting from centrifuging. Human biological material may include a pellet phase disposed in the retentate volume of the portable processing portable container apparatus, with the pellet phase comprising uncultured stromal vascular fraction cells separated from enzyme-digested cancellous bone material, wherein the stromal vascular fraction cells comprise osteoblasts and osteoclasts.

The portable container apparatus may be or have any feature or combination of features as described with respect to the first aspect of the disclosure. The pellet phase may be or have any feature of combination of features as described with respect to the first aspect of the disclosure.

A third aspect of the disclosure is provided by a method of preparing a medical treatment composition. The method comprises combining uncultured stromal vascular fraction cells separated from enzyme-digested cancellous bone material and biocompatible scaffold material suitable for administration to a human. The uncultured stromal vascular fraction cells comprise osteoblasts and osteoclasts. By uncultured, it is meant the stromal vascular fraction cells have not been multiplied be culturing following separation of the stromal vascular fraction cells from enzyme-digested cancellous bone material.

A number of feature refinements and additional features are applicable to the third aspect of the disclosure. These feature refinements and additional features may be used individually or in any combination. As such, each of the following features may be, but are not required to be, used with any other feature or combination of the third aspect or other aspects of the disclosure.

The uncultured stromal vascular fraction cells may be distinguished from stromal vascular fraction cells derived from human biological material other than cancellous bone material, for example from stromal vascular fraction cells derived from adipose tissue, by the presence of osteoblasts and osteoclasts. Such osteoblasts and osteoclasts are particularly beneficial for bone healing and bone repair applications. The uncultured stromal vascular fraction cells may be stromal vascular fraction cells from a pellet phase prepared according to the method of the first aspect of the disclosure for processing cancellous bone material.

The scaffold material may comprise a single material or a combination of materials, the scaffold material may comprise human biological material, which may or may not be from the same person as the source of the stromal vascular fraction cells. The scaffold material may comprise material that is not human biological material. The scaffold material may comprise one or any combination of two or more of the following: synovial fluid, fibrin clot material separated from human blood, spinal fluid, plasma from blood, platelet rich plasma from blood, bone fragments, hyaluronic acid, saline solution (e.g., a balanced saline solution, Hank's Balanced Solution) and a crystalloid solution (e.g., Lactated Ringer's solution). The scaffold material and/or the medical treatment composition may be in the form of a paste, for example a bone paste that may include bone fragments. The scaffold material and/or the medical treatment composition may be an injectable formulation.

For some implementations for treatments of knees and other joints, a preferred scaffold material may be or include synovial fluid as a major component. The synovial fluid may be from the joint of the same patient for an autologous procedure. The synovial fluid may be mixed with the cells and aqueous solution (e.g., Lactated Ringer's, Hank's Balanced Solution), which aqueous solution may be a suspension liquid in which the cells are suspended prior to mixing with the synovial fluid. The synovial fluid may be extracted from the joint of interest and may be filtered to remove larger particulate components before being mixed with the stromal vascular fraction cells.

For some implementations for vertebral disc applications, a preferred scaffold material may be or include as a major component fibrin clot material separated from human blood. The fibrin clot material may be separated from blood from the patient for an autologous procedure. The blood may be extracted from the patient and fibrin-creating components separated from the whole blood. The scaffold material may also include some aqueous solutions (e.g., Lactated Ringer's Solution, Hank's Balanced Solution), which aqueous solution may be a suspension liquid for suspension of the stromal vascular fraction cells prior to being mixed with the fibrin clot material.

For some implementations, the scaffold material may be or include as a major component bone graft material. The bone graft material may include ground bone from the patient for an autologous procedure, or may include acellular ground bone fragments, which may or may not be sourced from the patient. In some implementations, the scaffold material may include fragments of calcified bone recovered from the processing of the first aspect of the disclosure. The medical treatment composition may be in the form of a bone paste, for example for use to heal fractures or bone defects, which may or may not be the result of surgery. In some implementations, the medical treatment composition may be used following spine or neck surgery to promote quick and reliable bone healing, or may be used to assist healing of difficult fractures.

The medical treatment composition may include at least 200,000, at least 300,000, at least 500,000, at least 1,000,000 or at least 10,000,000 of the stromal vascular fraction cells. The medical treatment composition may often include up to 100,000,000, up to 50,000,000 or up to 10,000,000 of the stromal vascular fraction cells.

The medical treatment composition may include one or more components in addition to the stromal vascular fraction cells and the scaffold material. For example, the medical treatment composition may include a growth factor. A growth factor may promote tissue growth following administration of the stromal vascular fraction.

A fourth aspect of the disclosure is provided by a medical treatment composition that comprises uncultured stromal vascular fraction cells separated from enzyme-digested cancellous bone material and biocompatible scaffold material suitable for administration to a human.

A number of feature refinements and additional features are applicable to the fourth aspect of the disclosure. These feature refinements and additional features may be used individually or in any combination. As such, each of the following features may be, but are not required to be, used with any other feature or combination of the fourth aspect or other aspects of the disclosure.

The medical treatment composition may be prepared according to a method of the first aspect or the third aspect of the disclosure. The medical treatment composition may be or have any feature of combination of features as described with respect to the third aspect of the disclosure.

A fifth aspect of the disclosure is provided by a medical treatment product that comprises a syringe barrel having disposed therein a medical treatment composition. The medical treatment composition comprises uncultured stromal vascular fraction cells separated from enzyme-digested cancellous bone material and biocompatible scaffold material suitable for administration to a human.

A number of feature refinements and additional features are applicable to the fifth aspect of the disclosure. These feature refinements and additional features may be used individually or in any combination. As such, each of the following features may be, but are not required to be, used with any other feature or combination of the fifth aspect or other aspects of the disclosure.

The medical treatment composition may be prepared according to a method of the first aspect or the third aspect of the disclosure. The medical treatment composition may be or have any feature of combination of features as described with respect to the third aspect or fourth aspect of the disclosure.

A sixth aspect of the disclosure is provided by a medical treatment method that comprises administering to a human uncultured stromal vascular fraction cells separated from enzyme-digested cancellous bone material, the stromal vascular fraction cells comprising osteoblasts and osteoclasts.

A number of feature refinements and additional features are applicable to the sixth aspect of the disclosure. These feature refinements and additional features may be used individually or in any combination. As such, each of the following features may be, but are not required to be, used with any other feature or combination of the sixth aspect or other aspects of the disclosure.

The uncultured stromal vascular fraction cells as administered to the human may be in a medical treatment composition that may be or have any feature or combination of features described with respect to the third aspect, fourth aspect or other aspects of the disclosure. The administering may comprise ejecting the uncultured stromal vascular fraction cells from an injection device, which may for example be a medical treatment product of the fifth aspect of the disclosure. The administering may be to a location within or adjacent a joint, for example a knee joint or a hip joint. The administering may be to a location within or adjacent a bone defect or bone fracture. The administering may be to a location within the neck. The administering may be to a location within or adjacent the spine.

A seventh aspect of the disclosure is provided by a method for recovering a concentrate product comprising leuko stromal vascular cells separated from enzyme-digested cancellous bone material. The method includes directly aspirating from a portable container apparatus material of the pellet phase prepared from processing cancellous bone material in the portable container apparatus. The pellet phase material may be or have any feature or combination of any features described with respect to any other aspect of the disclosure. The pellet phase material may have been formed in the container by any method described with respect to any other aspect of the disclosure. The portable container apparatus may be or have any features of any portable container apparatus described herein with respect to any aspect of the disclosure.

Another aspect of the disclosure relates to compositions comprising uncultured stromal vascular fraction cells separated from enzyme-digested cancellous bone material for use for treatment to promote tissue growth. The treatment may be as described with respect to any other aspects of the disclosure. The treatment may be treatment of a tissue defect, for example a bone tissue defect or a defect of some tissue adjacent a bone. The tissue defect may, for example, be damaged tissue or a deficiency of tissue. The treatment may be for healing a wound or for treating for other tissue deficiencies. The treatment may be for tissue repair, such as at a location where there is damage to tissue. The tissue defect may be a result of natural causes, an accident or a medical procedure (e.g., radiation therapy, chemotherapy, surgical procedure). The treatment may be treatment for osteoarthritis. The medical treatment composition may be or include a feature or combination of features of a medical treatment composition as described with respect to the third aspect or fourth aspect of the disclosure. The use may be according to a medical treatment method of the sixth aspect.

Additional description concerning these and other aspects of this disclosure summarized above and various features thereof are provided in the figures and the discussions provided below.

BRIEF DESCRIPTION OF THE DRAWINGS

FIGS. 7A and 7B illustrate a translatable conduit in a portable container apparatus.

DETAILED DESCRIPTION OF PREFERRED EMBODIMENTS

Figure 1:
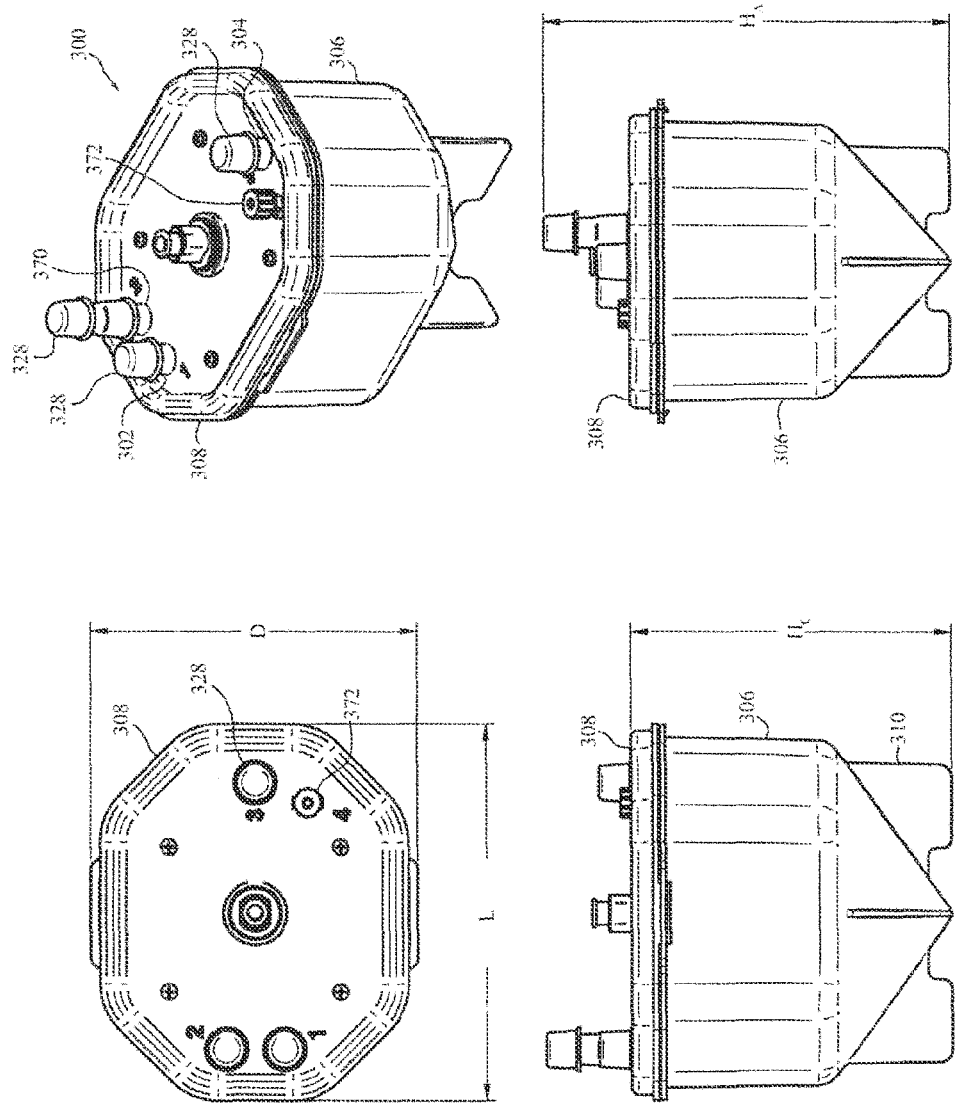
FIG. 1 shows top, perspective, side and end views of an embodiment of a portable container apparatus.

Reference is made to FIGS. 1-5 illustrating features of a portable container apparatus 300 for processing cancellous bone material. FIG. 1 shows top, front, side and perspective views of the apparatus 300 in an access orientation. The access orientation is a free-standing orientation in which the apparatus 300 would ordinarily be placed to introduce cancellous bone material into the apparatus 300 for processing. The apparatus 300 may also be placed in the access orientation during stages of processing after introduction of cancellous bone material into the apparatus 300. Accordingly, subsequent references to relative features of the apparatus 300, such as top, bottom, lower and upper, are relative to the apparatus 300 as in the access orientation as shown in FIG. 1. As illustrated in FIG. 1, the apparatus 300 has an apparatus height $H_A$, an apparatus length L, and an apparatus depth (or width) D. The apparatus 300 also includes a suction port 302 and an inlet port 304. The suction port 302 and inlet port 304 are disposed on the top of the apparatus 300 when the apparatus 300 is in the access orientation. In FIG. 1, the ports are illustrated as having caps 328 thereon. Such caps 328 are used to cover the various ports and may be removed and replaced as necessary during use of the apparatus 300.

The apparatus 300 includes a shell 306 and a lid 308. The shell 306 is a unitary bowl-like member where the only access into the interior, or cavity of the shell 306 is through the opening at the top of the shell 306. As illustrated in FIG. 1, this opening at the top of the shell 306 may be covered by the lid 308. The lid 308 and shell 306 may be rigid. The lid 308 and shell 306 are each preferably made of a clear polymeric material, such as a clarified polypropylene polymer composition, which provides low cellular adhesion and reasonable clarity. The lid 308 and shell 306 may be fabricated by injection molding. The lid 308 may be attached to the shell 306 in any appropriate manner, including snapping, clamping and/or gluing onto the shell 306. Together, the shell 306 and lid 308 form a container 322 with an internal containment volume 330 (see FIG. 5 and accompanying discussion below) within the apparatus 300. The internal containment volume 330 is the volume within the cavity of the shell 306 covered by the lid 308, and is the volume available for disposing both hardware and material to be processed in the container 322. This container 322 may have a container height $H_C$. The shell 306 may include a set of integral base supports 310 that may support the apparatus 300 in the access orientation when the apparatus 300 is placed on a horizontal surface. The apparatus height $H_A$ is larger than the container height $H_C$ by the distance of projections above the top of the container 322 for the inlet port 304, suction port 302, caps 328 and other upward projecting features described below. The shell 306 may be conveniently designed to efficiently fit within a centrifuge bucket. The projections above the container height $H_C$ may be configured so as not to interfere with operation of such a centrifuge. As seen in FIG. 1, the apparatus length L is equal to the container length and the apparatus depth is equal to the container depth (or width). As will be appreciated, the corresponding height, length and depth dimensions of the internal containment volume 330 will equal the height, length and depth dimensions of the container 322 less the corresponding thicknesses of walls of the shell 306 and lid 308. As shown in FIG. 1, some features may be integrally formed with the lid 308. For example as shown in FIG. 1 the suction port 302 and the inlet port 304 are integrally formed as a unitary fabricated piece with the lid 308. It should be appreciated that such features may be provided as separate pieces and then assembled, such as by gluing or other means. For structural integrity, fabrication as a unitary piece is generally preferred.

Figure 2:
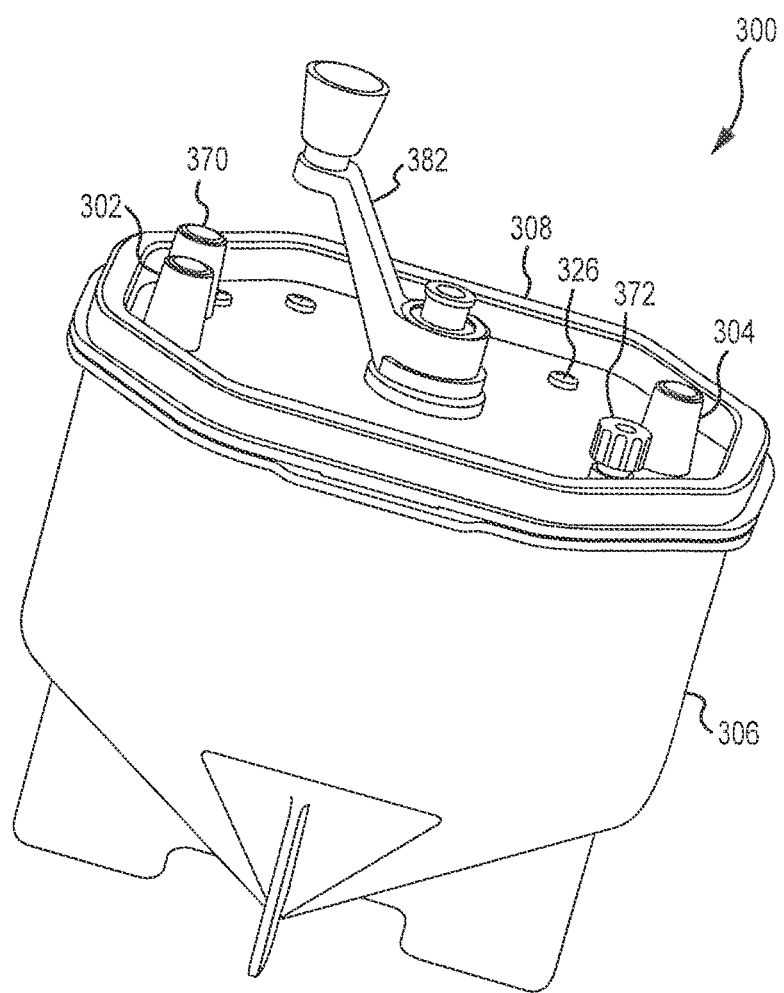
FIG. 2 shows another perspective view of the same portable container apparatus as FIG. 1.
Figure 3:
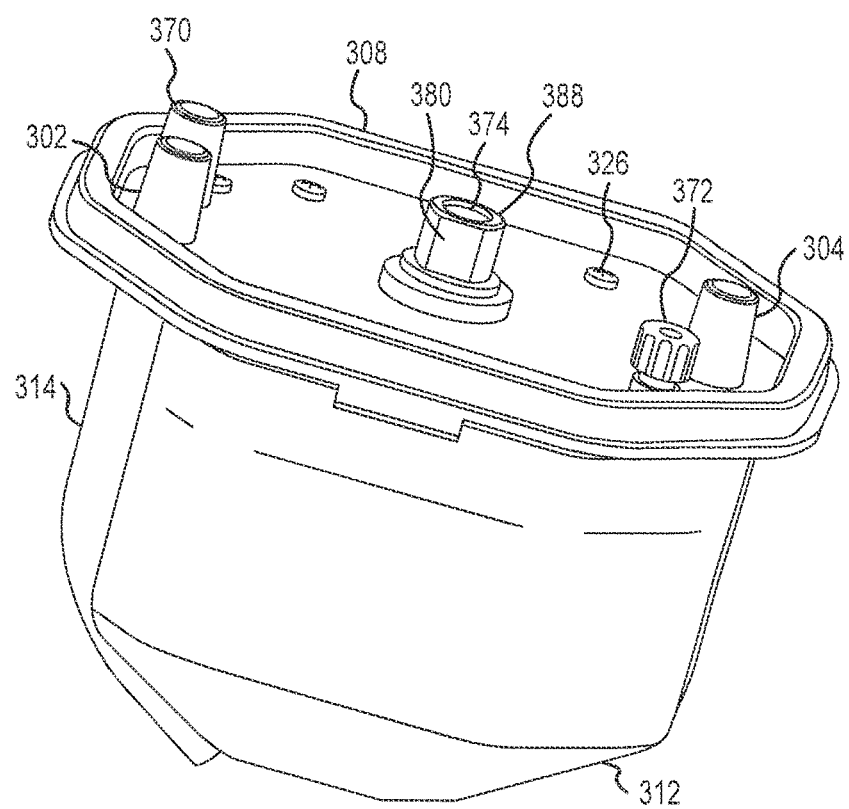
FIG. 3 shows the same portable container apparatus as FIG. 2 with a shell removed.

FIG. 2 shows another perspective view of the apparatus 300 with the caps 328 to ports removed and with an installed handle 382. FIG. 3 shows a portion of the apparatus 300 in the same orientation as in FIG. 2 with the shell 306 and handle 382 removed. With the shell 306 removed, a filter 312 can be seen that is disposed within the internal containment volume 330. The filter 312 may have a separation size, for example in a range from 70 microns to 800 microns. The filter is preferably made of a mesh material. The preferred mesh material is a nylon mesh. Also visible within the internal containment volume 330 is a suction port conduit 314 extending downward from the suction port 302. Additionally, as illustrated in FIG. 3, all components of the apparatus 300, except for the shell 306, are interconnected to the lid 308. In this regard, the subassembly shown in FIG. 3 may be assembled as shown and inserted into the shell 306.

Figure 4:
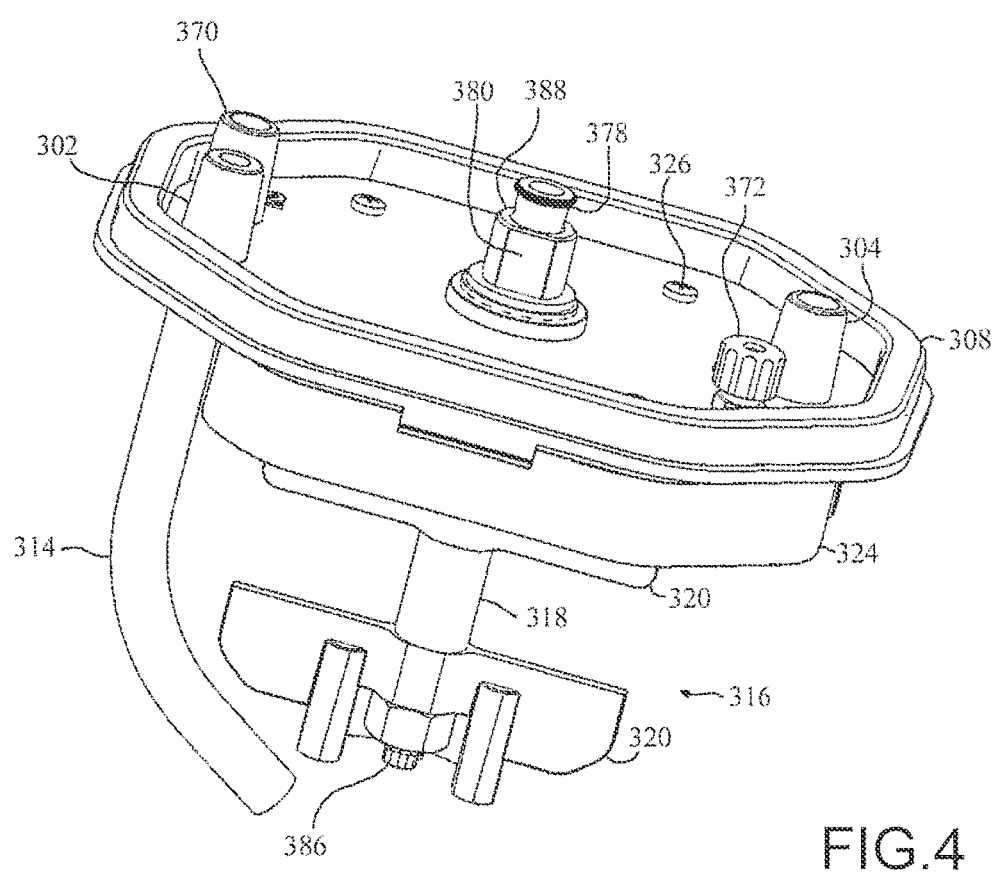
FIG. 4 shows the same portable container apparatus as FIG. 3 with a filter removed.

FIG. 4 shows another perspective view of a portion of the apparatus 300, in the same orientation as in FIG. 3 with both the shell 306 and the filter 312 removed. With the filter 312 removed, a flow barrier skirt 324 extending downward from the lid 308 into the internal containment volume 330 is visible. In an example, the flow barrier skirt may often extend between 5 mm and 50 mm downward from the lid 308. The flow barrier skirt 324 may serve as an attachment point for the filter 308 such that the filter 312 may be fixed relative to the lid 308. The flow barrier skirt 324 may also serve to prevent material from entering a tissue retention volume 332 (described below) and immediately moving through the filter 312 into the filtrate volume 334. The tissue retention volume 332 is that portion of the internal containment volume 330 contained within the filter 312 and barrier skirt 324 below the lid 308. The filtrate volume 334 is that portion of the internal containment volume 330 disposed outside of the filter 312 and barrier skirt 324. With the flow barrier skirt 324 in place, and material entering the inlet port 304 must at least move to below the lowest level of the flow barrier skirt 324 before it is able to pass through the filter 312 into the filtrate volume 334. The flow barrier skirt 324 may be part of a filter subassembly that includes the flow barrier skirt 324 and the filter 312. This subassembly is mounted to the lid 308 with four screws 326.

The filter 312 is asymmetric with respect to the lid 308 and shell 306 in that it is configured to provide clearance between its left side (as viewed in FIG. 3) and the shell 306 for the suction port 302 and suction port conduit 314. A portion of the filter 312 may be disposed about (e.g., rest on or around) a portion of the suction port conduit 314.

With the filter 312 removed (FIG. 4), a mixing device 316 can be seen. The mixing device 316 includes a rotatable shaft 318 and a set of mixing members 320. The axis of rotation of the rotatable shaft 318 may be through a central axis of the rotatable shaft 318. The mixing members 320 are in the form of paddles extending outward from the rotatable shaft 318. Accordingly, when the rotatable shaft 318 is rotated, the mixing members 320 will be rotated through the materials within the tissue retention volume 332 to aid in mixing the materials within the internal containment volume 330, and in particular within the tissue retention volume 332. The rotatable shaft 318 extends from outside of the internal containment volume 330 through the lid 308 to the inside of the internal containment volume 330. As the rotatable shaft 318 is rotatable relative to the lid 308, the mixing members 320 fixed to the rotatable shaft 318 are also rotatable relative to the lid 308. The rotatable shaft 318 may be made from a metal composition, such as stainless steel (e.g., grade 303, 304, or 316). Alternatively, the rotatable shaft 318 may be made from a high-strength polymer composition such as an Ultem™ resin product.

The rotatable shaft 318 may include a handle interface 380 (FIG. 3) that may provide an interface for the handle 382 (FIG. 2) to be interconnected to the portion of the rotatable shaft 318 outside of the internal containment volume 330. The handle interface 380 of FIG. 3 is in the form of a pair of parallel surfaces disposed about the portion of the rotatable shaft 318 outside of the internal containment volume 330. The handle 382 has a mating pair of interior parallel surfaces configured such that when the handle 382 is placed over the handle interface 380, turning the handle 382 will result in turning the rotatable shaft 318 and the mixing device 316. Such an interface 380 also allows for the handle 382 to be removed from and replaced on the handle interface 380 as needed during use of the apparatus 300.

Figure 5:
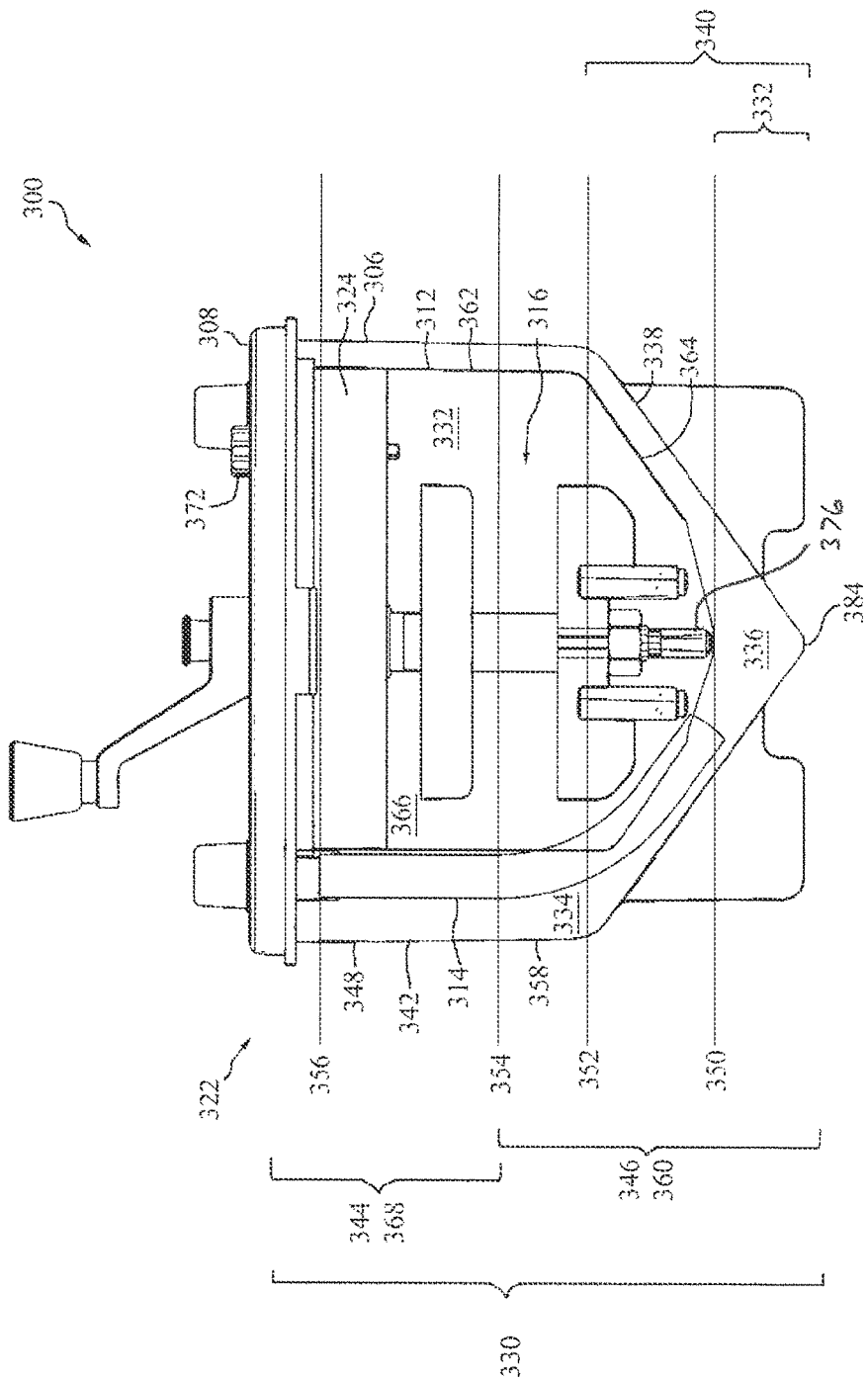
FIG. 5 illustrates various regions within the portable container apparatus of FIG. 1.

FIG. 5 is a side schematic view of the apparatus 300 showing the mixing device 316 and filter 312 within the shell 306. The internal containment volume 330 is the entire volume within the shell 306 and under the lid 308. Together, the portions of the shell 306 and lid 308 that contain the internal containment volume 330 are a container 322 of the apparatus 300. The filter 312 divides and separates the internal containment volume 330 of the container 322 into the tissue retention volume 332 disposed inside the filter 312, and a filtrate volume 334 disposed within the shell 306 on the outside of the filter 312. The filtrate volume 334 is that portion of the internal containment volume 330 into which filtrate enters after passing through the filter 312 from the tissue retention volume 332.

Disposed within the internal containment volume 330 at the bottom of the shell 306, below a level 350 that is at or below the lowest extent of the filter 312 (and therefore also below the lowest extent of the tissue retention volume 332), is a collection volume 336, such that the collection volume 336 is part of the filtrate volume 334 and occupies the lowermost portion of the filtrate volume 334.

The shell 306 has a tapered wall portion 338 that defines a tapered portion 340 of the internal containment volume 330, such that the cross-sectional area of the tapered portion 340 of the internal containment volume 330 tapers with a reducing cross-sectional area in a direction toward bottom of the container 322. By tapering, it means that the cross-sectional area in a horizontal plane (assuming the apparatus 300 is in the access orientation) becomes smaller in the direction of the taper (e.g., a direction orthogonal to the horizontal plane). The tapered portion 340 of the internal containment volume 330 occupies the portion of the internal containment volume 330 below a level 352 where the tapered wall portion 338 meets a straight wall portion 342 of the shell 306. The tapered wall portion 338 is shown as having a flat, uniform inclined wall surface. The incline angle of surfaces of the tapered wall portion need not be uniform from the top to the bottom of the tapered portion 340 of the internal containment volume 330, and may vary from top to bottom with portions having different incline angles, and may have a curved surface, provided that the cross-section area is reducing in the direction of the taper. Also, the tapered wall portion 338 need not be uniform around the perimeter of the tapered portion 340 of the internal containment volume 330. For example, in the embodiment in FIGS. 3-5, the tapered wall portion 338 has a steeper incline on the ends than on the front or back of the apparatus 300.

The shell 306 may comprise an upper portion 344 having a first wall surface portion 348 defining a corresponding upper portion 368 of the internal containment volume 330. Substantially all of the first wall surface portion 348 may have an incline relative to horizontal of at least 75°. For example, substantially all of the first wall surface portion 348 may be substantially vertical (90° incline relative to horizontal). The shell 306 may include a lower portion 346 located below the upper portion 344 and having a second wall surface portion 358 defining a corresponding lower portion 360 of the internal containment volume 330. The lower portion 360 may include the tapered wall portion 338 defining the tapered portion 340 of the internal containment volume 330. Substantially all of the tapered wall portion 338 may preferably have an incline relative to horizontal in a range of from 30° to 60°, although other angles or curved surfaces may be used. The tapered portion 340 of the internal containment volume 330 may occupy substantially the entire lower portion 360 of the internal containment volume 330. At least a first portion 362 of the filter 312 may be disposed in the upper portion 368 of the internal containment volume 330 and a second portion 364 of the filter 312 may be disposed in the lower portion 360 of the internal containment volume 330. The tapered wall portion 338 may form a nadir 384 at its lowest elevation. The nadir 384 may also be a nadir of the collection volume 336, the filtrate volume 334, the container 322, and the internal containment volume 330.

The internal containment volume 330 may include an available processing volume or "useable" volume 366 which may be the portion of the internal containment volume 330 that is usable and/or may normally be occupied by materials within the container 322 during normal use. For example, the available processing volume 366 may be the portion of the internal containment volume 330 below a level 356 that coincides with the bottom extension of a port through the lid 308 and that is not occupied by portions (e.g., internal hardware) of the apparatus 300 within the internal containment volume 330, such as the mixing device 316, barrier skirt 324, filter 312 and suction port conduit 314. The top of the available processing volume may be at the elevation of the bottom extension of the inlet port 304, which may define a maximum fill level within the internal containment volume 330.

The inlet port 304 in fluid communication with the tissue retention volume 332 through the lid 308 is configured for introducing cancellous bone material into the tissue retention volume 332. For example, the cancellous bone material may be introduced into the tissue retention volume 332 by expulsion from a syringe through the inlet port 304. An additional access port 372 in fluid communication through the lid 308 with the tissue retention volume 332 provides an additional route into the tissue retention volume 332, for example for introduction of additives.

The suction port 302 is in fluid communication through the lid 308 with the filtrate volume 334 via suction port conduit 314 extending from the suction port 302 to within the tapered portion 340 of the internal containment volume 330 in the vicinity of the top of the collection volume 336. The suction port 302 is configured for connection to a vacuum system, for example through connection of a suction conduit through which suction may be applied by a vacuum system to suction from the filtrate volume 334 material passing through the filter 312 from the tissue retention volume 332 into the filtrate volume 334.

The rotatable shaft 318 may include attached thereto a filter contact member 376 (FIG. 5) that is offset from an axis of rotation of the rotatable shaft 318. A lower end of the filter contact member 376 may contact a portion of the filter 312 as illustrated in FIG. 5. As the rotatable shaft 318 is rotated, the filter contact member 376 may rotate in a circular path about the axis of rotation of the rotatable shaft 318 remaining in contact with and moving along a portion of the filter 312. This contact may cause the filter 312 to deform and such deformation and/or the contact between the filter contact member 376 and filter 312 may cause materials that may have adhered to the filter 312 in this region to become dislodged from the filter 312. Thus, the filter contact member 376 may assist in keeping the filter from clogging and increasing the effectiveness of the filter 312.

The rotatable shaft 318 may include a lumen 374 therethrough. The top of the lumen 374 is visible in FIG. 3 and the bottom of the lumen 374 is at the opposite end of the rotatable shaft 318. The lumen 374 may have a distal end 386 (FIG. 4) within the tissue retention volume 332 and a proximal end 388 (FIGS. 3 and 4) outside of the internal containment volume 330 and thus may allow access to the tissue retention volume 332 therethrough. The lumen 374 may be disposed along the central axis of the rotatable shaft 318. The lumen 374 thus provides a conduit for accessing the internal containment volume 330. As further described below, the lumen 374 may provide access for removing processed material from the internal containment volume 330. In that respect, the opening through the lid 308 through which the rotatable shaft 308 extends acts as an extraction port through which access is provided via the lumen 374 that passes through such opening. The apparatus 300 may include a plug 378, shown in FIG. 4 and not shown in FIG. 3, that may be placed in the proximal end 388 of lumen 374 to seal the lumen 374.

Figure 6:
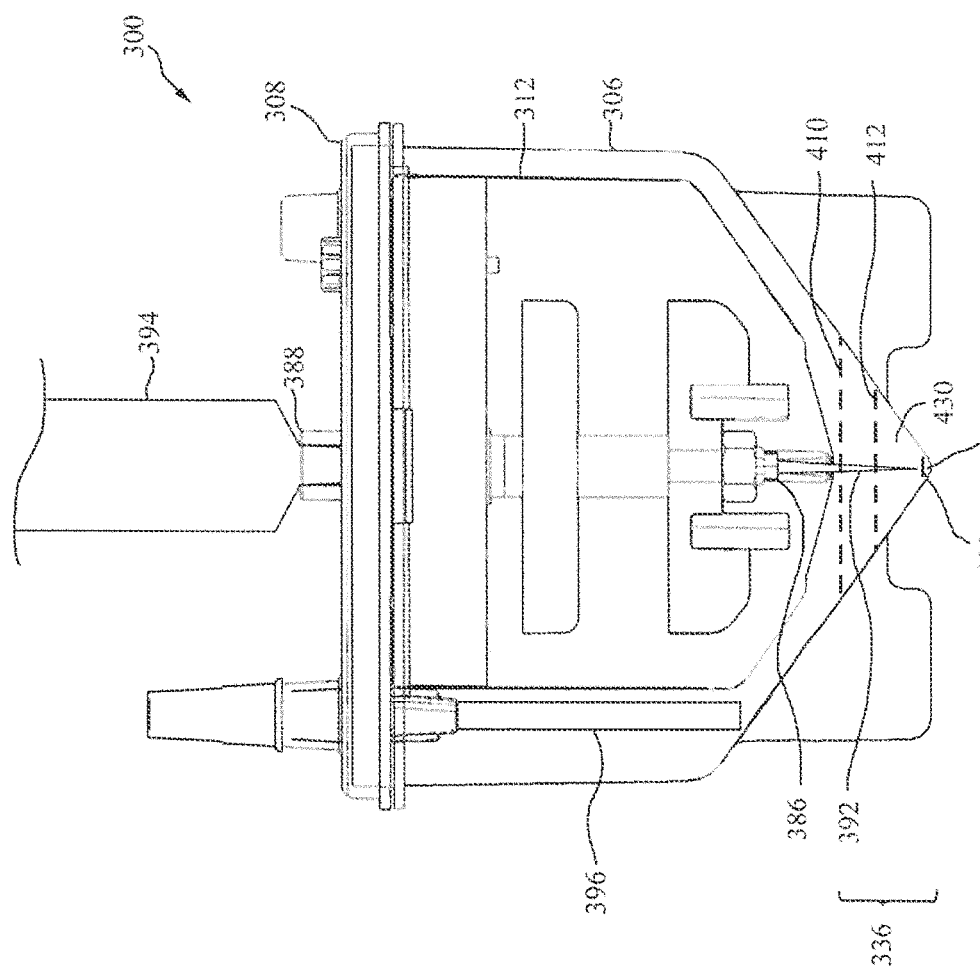
FIG. 6 illustrates a needle inserted into a portable container apparatus.

As shown in FIG. 6, a hypodermic needle 392 may be inserted through the lumen 374 and may be advanced out of the distal end 386 of the lumen 374 and to pierce through the filter 312 to directly access the collection volume 336 (the volume under the line 410 in FIG. 6). Thus, the hypodermic needle 392 may be used to inject material into, or remove material from the collection volume 336. Additionally, as the axis of the lumen 374 is vertically oriented, access to the collection volume 336 using the hypodermic needle 392 is by downward vertical insertion into the lumen 374 from above the portable container apparatus. Such vertical insertion coupled with the ability of the apparatus 300 to be placed on a flat surface in the access orientation, allows for user-friendly access to the collection volume 336, and helps avoid complications that could compromise operations to collect valuable processed material from the collection volume 336.

The hypodermic needle 392 may be interconnected to a syringe 394. The proximal end 388 of the lumen 374 may include a tapered receptacle adapted to mate with a tapered tip of the syringe 394. In this regard, as shown in FIG. 6, the depth of penetration by the hypodermic needle 392 into the collection volume 336 when the tapered tip of the syringe 394 is in contact with the tapered receptacle of the lumen 374 may be controlled by controlling the length of the hypodermic needle 392 extending from the syringe 394. Additionally, the proximal end 388 of the lumen 374 may include a feature, such as a notch, to retain an o-ring (not shown) such that when the syringe 394 is positioned against the proximal end 388 of the lumen 374, the o-ring forms a seal between the proximal end 388 of the lumen 374 and the syringe 394 (i.e., a seal through the o-ring between a wall surface in the tapered receptacle and an exterior wall surface of the tip of the syringe inserted into the tapered receptacle).

Referring to FIGS. 7A and 7B, the second suction port 370 includes a translatable member 396 that may be translated up and down relative to the lid 308 to vary the depth (elevation within the filtrate volume 334) at which material from the filtrate volume 334 is drawn through the second suction port 370. Examples of the various depths (elevations) at which the translatable member 396 may be positioned are illustrated in FIGS. 7A, 8, 9 and 11 and are discussed below in relation to methods of using the apparatus 300. The fit between the translatable member 396 and the opening through the lid 308 of the second suction port 370 is such that the translatable member 396 may be readily translated up and down to a desired level, while maintaining a tight enough fit to allow a vacuum applied to the translatable member 396 to adequately draw material out of the filtrate volume 334.

In general, the parts discussed with reference to the apparatus 300 may be made from any appropriate biocompatible material. In particular, the shell 306 may be made from a biocompatible transparent polymer material to allow inspection of the contents therein. Screws 326 and the rotatable shaft 318 may be made from metal, such as stainless steel. Other parts of the assembly 300 pictured in FIG. 1 may be made from appropriate biocompatible polymers.

In a method for processing cancellous bone material using the apparatus 300, cancellous bone material may be processed within the internal containment volume 330 to prepare within the apparatus 300 a concentrated product comprising stromal vascular fraction cells from the cancellous bone material. Cancellous bone material to be processed may be introduced into the tissue retention volume 332 through the inlet port 304. Processing operations performed using the apparatus 300 comprise washing, which involves adding aqueous wash liquid to the internal containment volume 330 to contact cancellous bone material disposed in the tissue retention volume 332. Optionally, the washing may include centrifuging the apparatus 300 following contact between the wash liquid and the cancellous bone material. After washing, the method may comprise digesting, which may include adding to the portable container apparatus a digestion medium. After the digestion, the method may include centrifuging the apparatus 300 to prepare in the collection volume 336 a concentrate product, for example in a pellet phase, concentrated in stromal vascular fraction cells from the cancellous bone material.

During the washing, the wash liquid may be added to the internal containment volume 330 to contact cancellous bone material within the tissue retention volume 332 and with at least a portion, preferably a majority, and more preferably most, of the wash liquid passing through the filter 312 into the filtrate volume 334.

The wash liquid may wash one or more components from the cancellous bone material while retaining washed cancellous bone material in the tissue retention volume 332. The washed cancellous bone material may be retained in the tissue retention volume 332 by the filter 312. Wash liquid passing into the filtrate volume 334 may be removed from the filtrate volume 334, along with any component or components washed from the cancellous bone material that pass through the filter 312 from the tissue retention volume 332. Optionally, after adding the wash liquid, the apparatus 300 may be centrifuged to facilitate a high degree of separation of the wash liquid from the cancellous bone material retained in the tissue retention volume 332. Next, the wash liquid may be removed from the filtrate volume 334 by suctioning through the suction port 302 of the apparatus 300. The washing may include multiple wash stages. During the washing, the mixing device 316 may be rotated by rotating the handle 382 to mix contents of the internal containment volume and assist the washing process.

During the digestion, an enzyme, such as for example collagenase, may be added to the internal containment volume 330 through the additional access port 372 or through the inlet port 304. The enzyme may be added to the apparatus 300 in a digestion medium to contact at least a washed portion of the cancellous bone material that may remain in the tissue retention volume 332 following the washing. During the digesting, the mixing device 316 may be rotated to assist in the digesting process.

After adding the enzyme, the digesting may comprise agitating contents of the containment volume of the apparatus 300 for a time and at a temperature sufficient for the digestion to proceed to an extent to significantly release the stromal vascular fraction cells and permit the cells to pass through the filter 312. The agitating may involve any method to agitate contents of the internal containment volume 330, including for example one or both of: (a) shaking the apparatus 300 to agitate the contents within the apparatus 300 and (b) mixing the contents within the apparatus 300 by rotating the mixing device 316 using the handle 382.

Figure 8:
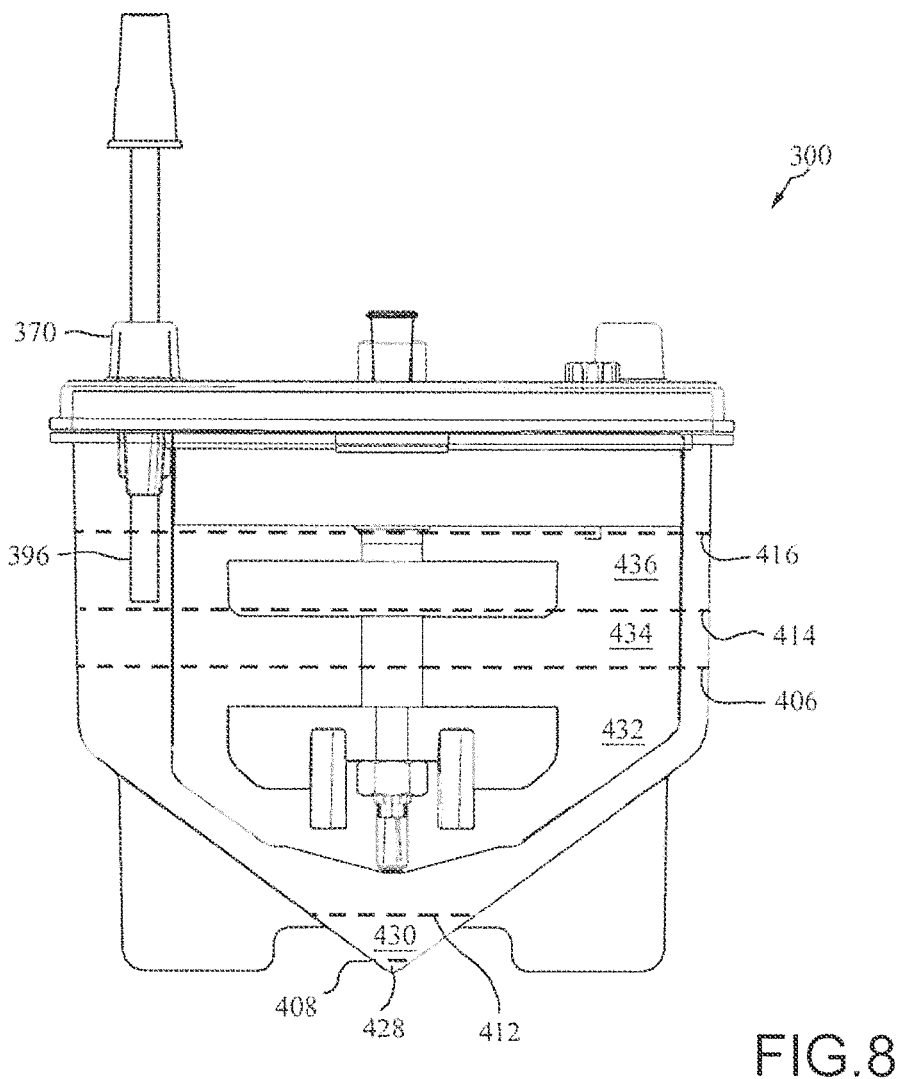
FIGS. 8-11 illustrate various operations in a method of processing cancellous bone material within a portable container apparatus.

Post-digestion centrifuging promotes separation of the stromal vascular fraction cells from other components of the digested cancellous bone material and passage of the stromal vascular fraction cells through the filter 312 for collection in the collection volume 336. FIG. 8 illustrates an example of multiple material phases that may collect within the filtrate volume 334 as a result of centrifuging. In the example of FIG. 8, the first (bottom) material phase may be a small layer of red blood cells 428 located in the region of the filtrate volume 334 below the line 408. This volume below the line 408 occupies a bottom portion of the collection volume 336, and in many situations may even not be present or may be so small as to be indistinguishable. The second material phase may be a stromal vascular fraction layer 430 from cancellous bone material and may be located in the region of the filtrate volume 334 below the line 412 and above the line 408. As will be appreciated, the red blood cell layer 428 and the stromal vascular fraction layer 430 may not be divided by a sharp line, and the blood cell layer 428 may grade into the lower portion of the stromal vascular fraction layer 430. This volume below the line 412 and above the line 408 also occupies a portion of the collection volume 336. The stromal vascular fraction layer 430, or the stromal vascular fraction layer 430 together with the red blood cell layer 428, may be in the form of a pellet, and may be referred to as a pellet phase. The layer 428 and/or the layer 430 may also include some very small bone fragments that may have passed through the filter 312 into the filtrate volume 334 during processing. A third example material phase may be an aqueous layer that occupies the region of the filtrate volume 334 below the line 406 and above the line 412. A fourth example material phase is shown as layer 434 that occupies the region of the filtrate volume 334 below the line 414 and above the line 406. Such a layer 434 may contain desegregated fatty tissue components. A majority of calcified bone component from the original cancellous bone material will generally collect and be retained on the filter 312, except for very small bone fragments that may have passed through the filter 312 during processing. The calcified bone component retained on the filter may be in the form of pieces or fragments of calcified bone that were unable to pass through the filter 312 during centrifuging. A fifth example material phase may be an oil layer 436 that occupies the region of the filtrate volume 334 below the line 416 and above the line 414. The separated phase layers as shown are provided to illustrate relative positioning and are not intended to represent an actual scale of the relative sizes of the phases, except that the red blood cell layer 428 and stromal vascular fraction layer 430 are contained within the collection volume 336 and the other layers may extend above the collection volume 336. As will be appreciated, the material phases 428, 430, 432, 434 and 436 are in order of decreasing density, with the layer 428 being the most dense phase and with the layer 432, the layer 434 and the layer 436 all being less dense than the stromal vascular fraction layer 430. Also, not all of these layers may be present in all situations and in other situations it is possible that other layers may also be present. For example, the layer 434 may be absent if bone marrow and other fatty tissue-containing components are thoroughly washed from the cancellous bone material during washing operations.

Figure 9:
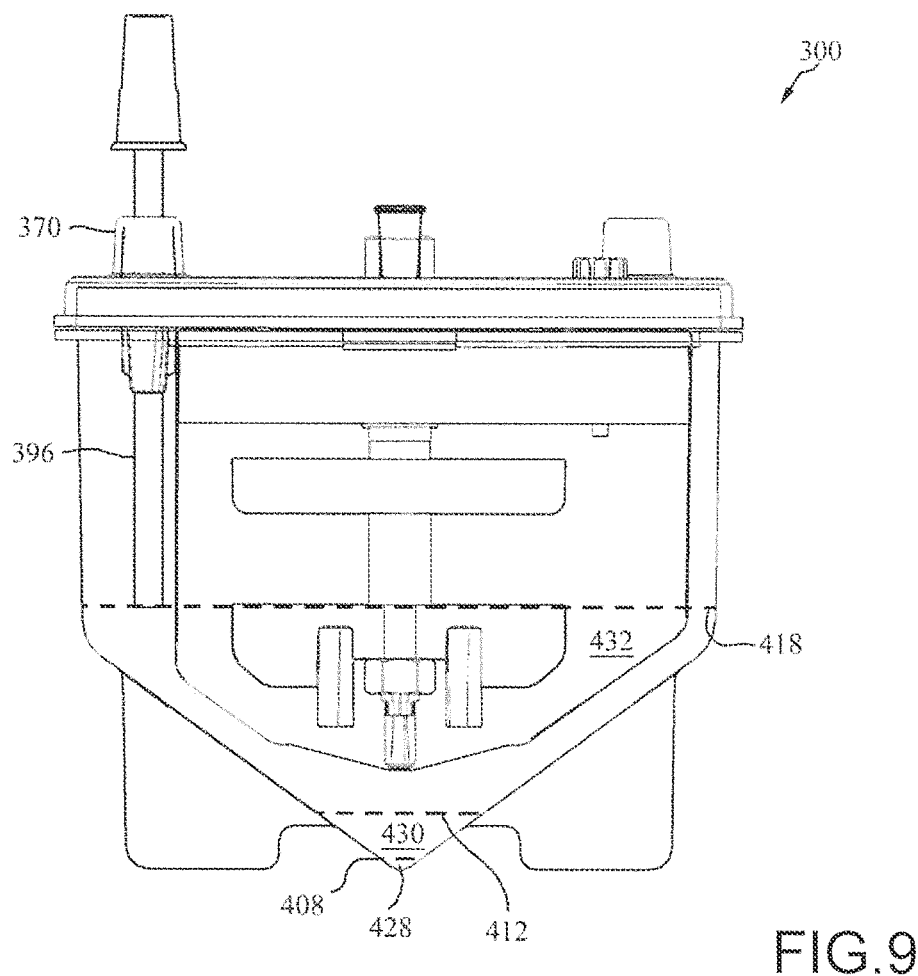

The translatable member 396 of the second suction port 370 may be employed to first remove the layer 436, then to remove the layer 434, and then to remove the layer 432. As illustrated in FIG. 8, the translatable member 396 may be positioned such that the end of the translatable member 396 is disposed within the layer 436. Suction applied to the translatable member 396 will remove the fluid of layer 436. As fluid is removed, the translatable member may be lowered to remove additional fluid down to a desired level, which may be removal of all or most of layers 436, 434 and 432. For example, once layer 436 has been removed, the translatable member 396 may be lowered into the layer 434 and then into the aqueous layer 432 for sequential removal of these layers. FIG. 9 illustrates the aqueous layer 432 partially removed (after already removing the top layers 436 and 434 such that the top of the aqueous layer 432 is at line 418). As another example, the translatable member 396 may be initially inserted to the position shown in FIG. 9 and suction applied until a portion of the layer 432 is removed and also the layer 434 and layer 436 are removed above line 418, resulting in the arrangement of FIG. 9.

Figure 10:
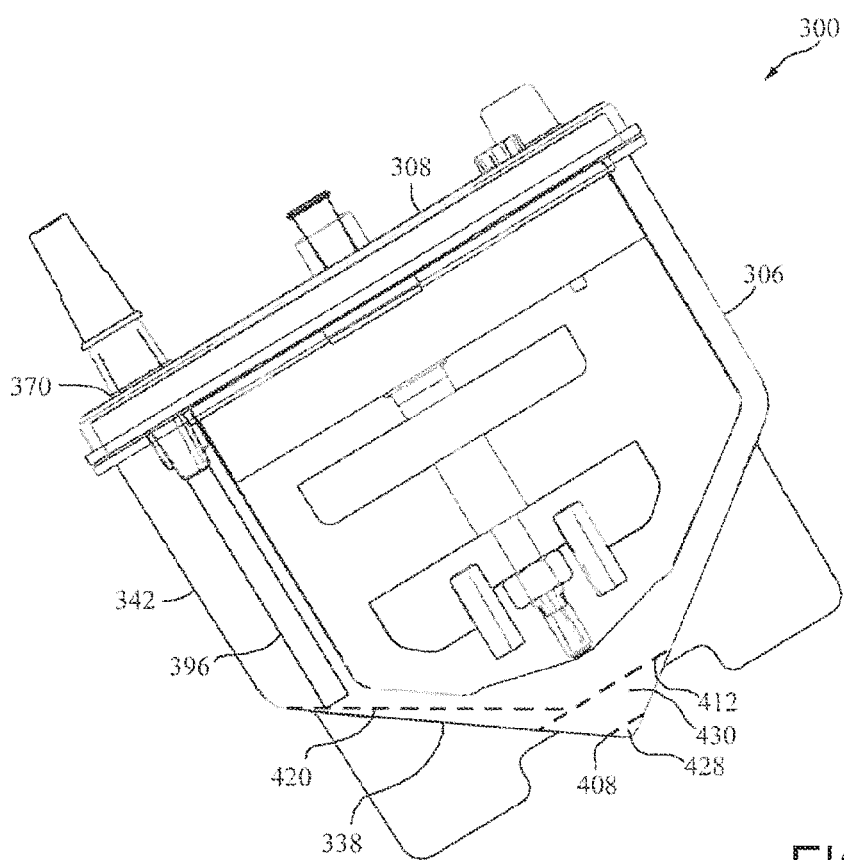
Figure 11:
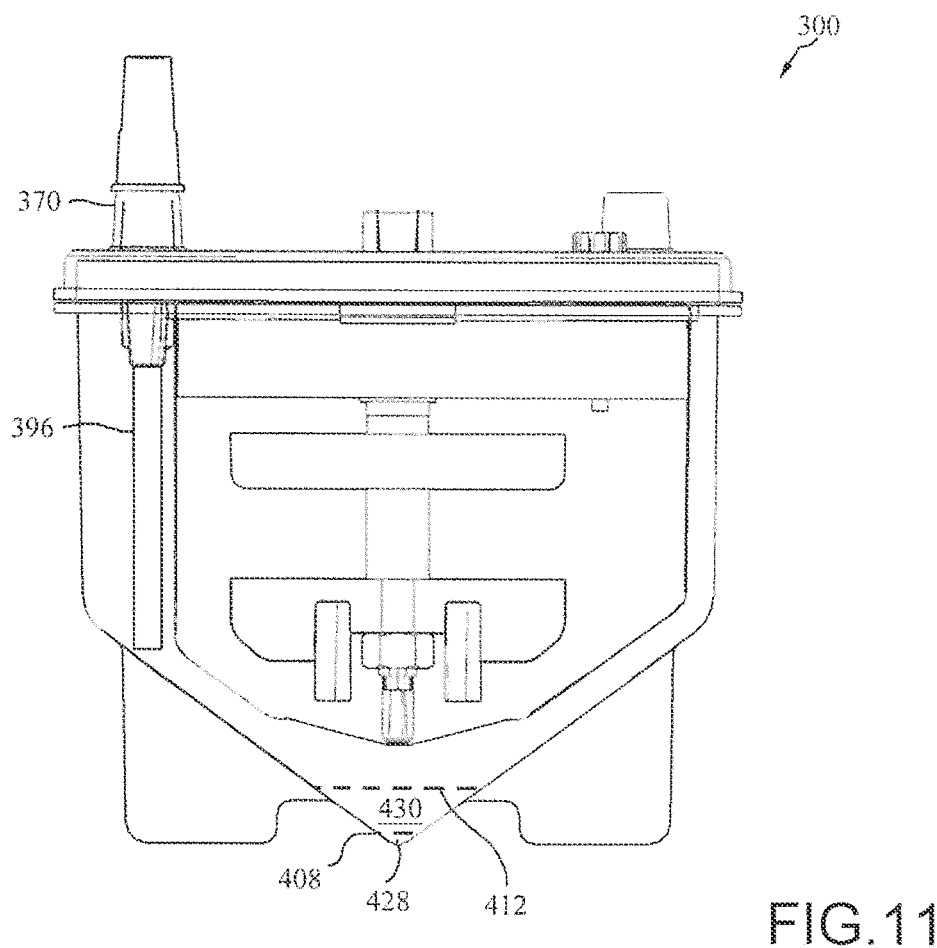

Once fully inserted into the filtrate volume 334, the translatable member 396 may not be operable to remove a portion of the layer 432 while the apparatus 300 is in the access orientation. Accordingly, a user may gently tilt the apparatus 300 as illustrated in FIG. 10 to further remove the more of layer 432. As illustrated, the stromal vascular fraction layer 430 below the line 412 may form a pellet which may retain its position as the apparatus 300 is tilted. This attribute of the pellet allows the apparatus 300 to be tilted such that fluid of the layer 432 flows laterally toward the translatable member 396 disposed proximate to the interface between the tapered wall portion 338 of the shell 306 and the straight wall portion 342 of the shell 306 as illustrated by line 420 in FIG. 10. Such tilting may allow suction to be applied to the layer 432 without the suction substantially affecting the stromal vascular fraction layer 430, which remains in place and stationary relative to the container of the apparatus 300. Once the aqueous layer 432 has been satisfactorily removed, the apparatus 300 may be returned to its access orientation, as shown in FIG. 11, for removal of the stromal vascular fraction 430 from the collection volume 336.

To remove material of the pellet phase after the less-dense material phases have been removed from above the pellet phase the hypodermic needle 392 attached to the syringe 394 may be inserted into the collection volume 336 as illustrated in FIG. 6 and a diluent fluid (e.g., suspension liquid) may be injected into the collection volume 336 such that the diluent fluid, stromal vascular fraction layer 430 and red blood cell layer 428 together occupy at least a portion of the collection volume 336 under line 410, and are preferably limited to being present only in the collection volume 336 and do not occupy space above line 410. After injection of the diluent fluid, a user may gently tap the apparatus 300 against a hard surface to cause the diluent fluid to mix with the stromal vascular fraction and the layer of red blood cells. A second hypodermic needle may then be inserted through the lumen 374 and the diluent/stromal vascular fraction/red blood cell mixture may be removed from the apparatus 300, for example by drawing the mixture through the hypodermic needle and into a syringe, to complete the selective removal of material of the pellet phase from the container 322 relative to other less-dense material phases.

An alternative technique to remove material of the pellet phase after the less-dense material phases have been removed from above the pellet phase, is to insert the hypodermic needle 392 such as shown in FIG. 6 into the pellet phase. The pellet phase may then be directly aspirated through the hypodermic needle 392 into the syringe 394, to complete selective removal of material of the pellet phase from the container 322 relative to the other, less-dense material phases. In this way, the material of the pellet phase may be removed from the container 322 without suspending material of the pellet phase in a suspension liquid.

As a further processing alternative, the material of the pellet phase (red blood cells layer 428 and stromal vascular fraction 430) may be removed from the container 322 without first removing the less-dense material phases (layer 432, layer 434 and layer 436), or without removing all of those less-dense material phases. For example, a hypodermic needle (similar to FIG. 6) may be inserted through the lumen 374 while some or all of the less-dense material phases remain in the container 322, with the distal tip of the needle disposed in the pellet phase (similar to FIG. 6) and the material of the pellet phase may then be directly aspirated through the hypodermic needle and into a syringe in fluid communication with the hypodermic needle. This technique may permit selective removal of the material of the pellet phase from the container 322 without first removing the less dense-material phases and without suspending the material of the pellet phase in a suspension liquid. After removal of the material of the pellet phase, the less-dense material phases may remain inside the container 322. Removal by such a technique significantly simplifies processing, because the processing associated with removing the less-dense material phases (including tapping the container) may be eliminated, reducing potential processing errors and potential loss of target cells to adhesion to container or equipment surfaces.

Figure 12:
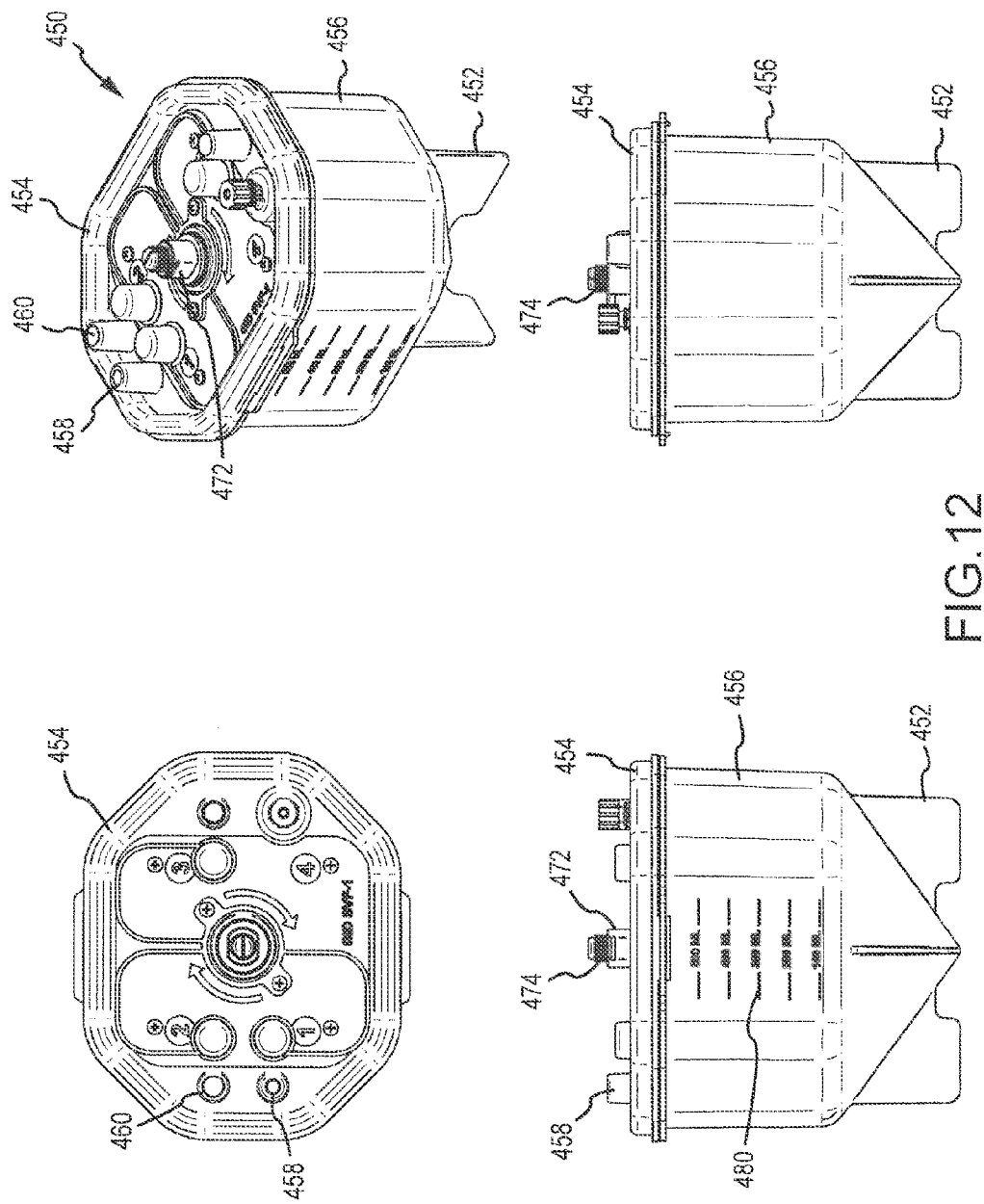
FIG. 12 shows top, perspective, side and end views of another embodiment of a portable container apparatus.
Figure 13:
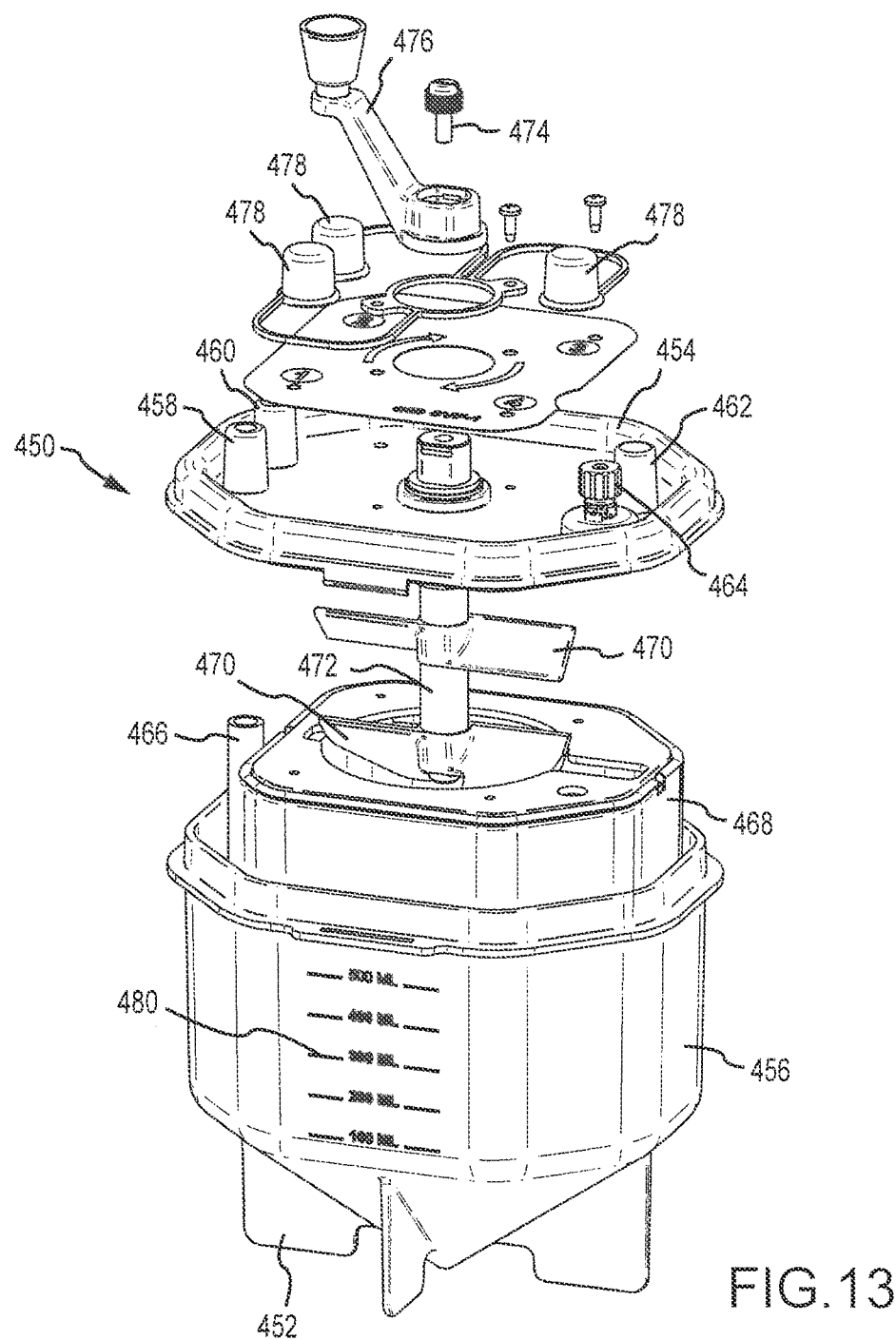
FIG. 13 shows an exploded view of the same portable container apparatus as FIG. 12.

Referring now to FIGS. 12 and 13, another embodiment is shown for a portable container apparatus. As shown in FIGS. 12 and 13, a portable container apparatus 450 has an access orientation in a freestanding, upright position as supported by base supports 452. The apparatus 450 includes a lid 454 covering a bowl-like shell 456, which make up a container having an internal containment volume under the lid 454 within the shell 456. The apparatus 450 includes a first suction port 458, a second suction port 460, an inlet port 462 and an auxiliary access port 464, which may be generally as describes for similar features of the apparatus 300 described with respect to FIGS. 1-7.

The first suction port 458 is connected with a suction conduit 466 extending from the first suction port 458 to within a tapered portion of an internal containment volume of the apparatus 450. The second suction port 460 is adapted to receive a translatable suction conduit, similar to the translatable member 396 described with respect to FIG. 7. The apparatus 450 includes a filter 468 suspended from the lid 454 and which divides the internal containment volume in the apparatus 450 between a tissue retention volume disposed inside the filter 468 and a filtrate volume disposed on the other side of the filter 468. The apparatus 450 includes a rotatable mixer disposed within the filtrate volume that includes propellers 470 connected to a rotatable shaft 472, which may be rotated to operate the rotatable mixer and cause the impellers 470 to mix and circulate fluid within the internal containment volume of the apparatus 450. The propellers 470 may alternatively be referred to as impellers or mixing impellers. The rotatable shaft 472 includes an internal lumen that extends from a proximal end outside of the container of the apparatus 450 to a distal end in the tissue retention volume, to permit access into the internal containment volume in a manner similar to that discussed previously for the apparatus 300 shown in FIGS. 1-7. A removable plug 474 may be disposed in a proximal end of the lumen for sealing the lumen when the lumen is not in use. The rotatable shaft includes a handle interface which may be interfaced with a hand-manipulable handle 476 (FIG. 13) to operate the rotatable mixer. The rotatable mixer is designed for primary operation by rotating the handle in a clockwise direction, as indicated by the directional arrows on a plate as shown in FIG. 13. The apparatus 450 includes attached caps 478 which may used to cap the first suction portion 458, second suction port 460 and inlet port 462 as needed, such as to seal the container for transportation between processing locations or during agitation on a warmer-shaker during digestion operations. The apparatus 450 is operable substantially in the same way as described previously for the apparatus 300 shown in FIGS. 1-7. The apparatus 450 includes volume gradation markings 480 that indicate the volume contained within the tissue retention volume (within the filter 468) up to different elevations of the container 450 when in the access orientation.

With continued reference to FIGS. 12 and 13 features of one or both of the propellers 470 may be configured to assist mixing of contents within the portable container apparatus and to reduce potential for plugging of the filter 468. One or both of the propellers 470 may have pitched blades that direct flow of fluid from the respective propeller 470 in an axial direction relative to the axis of rotation of the rotatable shaft 472. As shown in FIG. 13, the configuration of the bottom propeller 470 may include impeller blades 494 that are pitched at an angle that will propel fluid flow in an upper axial direction along the rotatable shaft 472 when the rotatable shaft 472 is rotated in the clockwise rotational direction. This type of upward pumping action by the bottom propeller 470 may assist in moving material from the filter 468 to help keep the filter 468 from plugging. In similar manner, the top propeller 470 may have pitched blades 493 that propel fluid flow in an axial direction upward toward the underside of the lid 454 and away from the tissue collector 482 when the rotatable shaft 472 is rotated in the clockwise rotational direction. This upward pumping action by the top propeller 470 may assist in further pulling material up and away from the filter 468 to help prevent plugging of the filter 468.

In one enhancement, one or more of the blades 494 may be configured to scrape at least a portion of the filter 468 when the rotatable shaft 472, and thus also the bottom propeller 470, is rotated in the clockwise rotational direction. Such scraping of the filter 468 may be accomplished by configuring an edge portion 495 of a blade 494 to contact and scrape surfaces of the filter 468. In that regard, a blade may be configured with a slanted lower edge shaped to correspond with and contact a corresponding tapered portion of the filter 468. A leading edge of the blade 494 may have a tapering width to assist in scraping tissue or other material away from the surface of the filter 468. For example, the configuration of the blade 494 may include a beveled surface toward a leading edge of a slanted edge portion that contacts the filter 468 that may help to lift tissue or other material away from the filter 468 when the lower propeller 470 is rotated in the clockwise rotational direction.

Figure 14:
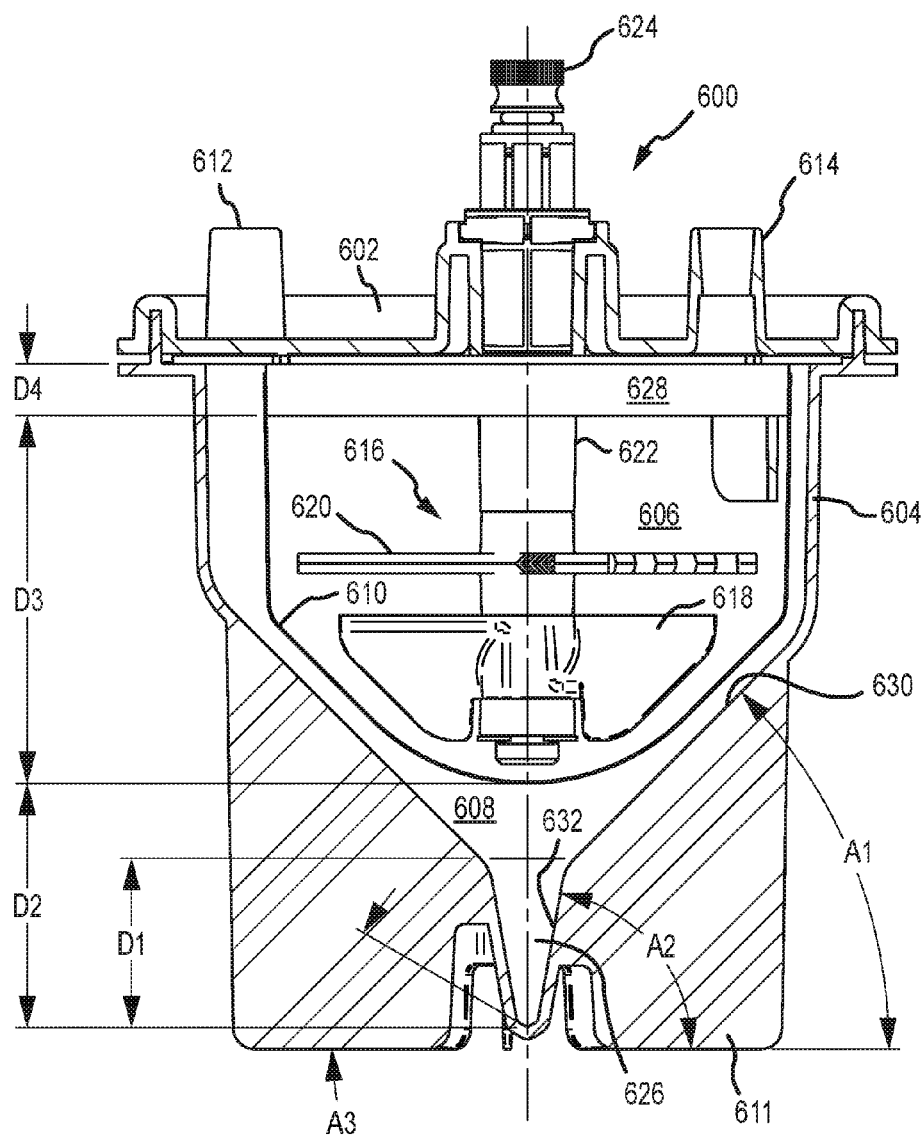
FIG. 14 shows a sectional view of another embodiment of a portable container apparatus including a pellet well.

Reference is made to FIG. 14, which shows another embodiment for a tissue collection and processing apparatus. FIG. 14 shows an apparatus 600 including a lid 602 and a shell 604 that form a container having an internal containment volume including a tissue retention volume 606 and a filtrate volume 608 disposed on different sides of a filter 610. The apparatus 600 is shown in an access orientation as it would be supported by base supports 611 that are integrally formed with the shell 604. A suction port 612 is in fluid communication with the filtrate volume 608 and through which material may be removed from the filtrate volume 608. An inlet port 614 is provided for introducing tissue or other material into the tissue retention volume 606. The apparatus 600 may include additional access ports (e.g., additional suction port, auxiliary port), such as described for previous embodiments. The apparatus 600 includes a rotatable assembly 616 including a mixing impeller 618 and a tissue collector 620. The mixing impeller 618, tissue collector 620 and a spacer 622 are mounted on a rotatable shaft (not shown) that extends from above the container through the lid 602 and into the tissue retention volume 606. The rotatable shaft includes a central lumen that extends through the rotatable shaft from outside the container and opens at the bottom of the mixing assembly near the bottom portion of the tissue retention volume 606 just above the filter 610.

The lumen is accessible by removing a cap 624. The lid 602, shell 604, tissue retention volume 606, filtrate volume 608, filter 610, base supports 611, suction port 612, inlet port 614, rotatable shaft and mixing impeller 618 may have any design features or configurations as described previously in relation to corresponding features of the apparatus described in any of FIGS. 1-13. The apparatus 600 includes a pellet well 626 at the bottom of the filtrate volume 608, as discussed further below.

The tissue collector 620 may help collect any stringy tissue components within the tissue retention volume 606 to prevent such stringy tissue components from plugging the filter 610. Typically, cancellous bone material will not include problematic stringy tissue components, and in a design variation the apparatus 600 may be modified to not include the tissue collector 620. However, presence of the tissue collector 620 is not detrimental to use of the apparatus 600 for processing cancellous bone material.

In some preferred implementations the mixing impeller 618 may be configured with pitched blades for producing axially upward flow when the rotatable shaft is rotated in an appropriate direction. The blades of the mixing impeller 618 may beneficially be designed with portions that scrape the filter 610 as the rotatable shaft 616 is rotated, in a manner similar as described above with respect to FIGS. 12 and 13. The lumen through the rotating shaft may be aligned with a collection volume located in the filtrate volume 608 below the bottom of the filter 610, and may provide access for convenient removal of processed material from the pellet well 626 in the collection volume located below the filter 610.

Various example dimensions are shown for the apparatus 600. A first height dimension $D_1$ shows the vertical dimension from the bottom of the collection volume at a nadir of the filtrate volume 608 to a top elevation of the pellet well 626 within the collection volume. Second height dimension $D_2$ shows the vertical dimension from the bottom to the top of the collection volume that is below the filter 610. The bottom elevation of the collection volume also corresponds with the bottom elevation of the pellet well 626. Third height dimension $D_3$ shows the vertical dimension from the bottom of the filter 610 to the bottom of a skirt 628 from which the filter 610 is suspended. Fourth height dimension $D_4$ shows the vertical extent of the skirt 628. Angle $A_1$ is an angle between horizontal and a first tapered interior wall surface 630 of the container that defines at least a portion of the filtrate volume 608, including defining at least a portion of the collection volume. Angle $A_2$ is an angle from horizontal to a second tapered interior wall surface 632 of the container that defines at least a portion of the pellet well. Angle $A_3$ is an angle between horizontal and a third tapered interior wall surface of the container that defines at least a bottom portion of the pellet well 626. Example dimensions for one example implementation for the embodiment of the apparatus 600 includes 25.7 millimeters for $D_1$, 37.1 millimeters for $D_2$, 55.9 millimeters for $D_3$, 7.9 millimeters for $D_4$, 45° for $A_1$, 80° for $A_2$, and 30° for $A_3$. Such an example may be designed for example to include an internal containment volume of about 270 cubic centimeters and a volume in the pellet well 626 of about 1.2 cubic centimeters, and with the filtrate volume 606 configured to accommodate processing of up to about 110 cubic centimeters of cancellous bone material in the tissue retention volume 606 for preparation of a pellet phase including leuko stromal vascular fraction concentrate that may fill or nearly fill the pellet well 626.

Figure 15:
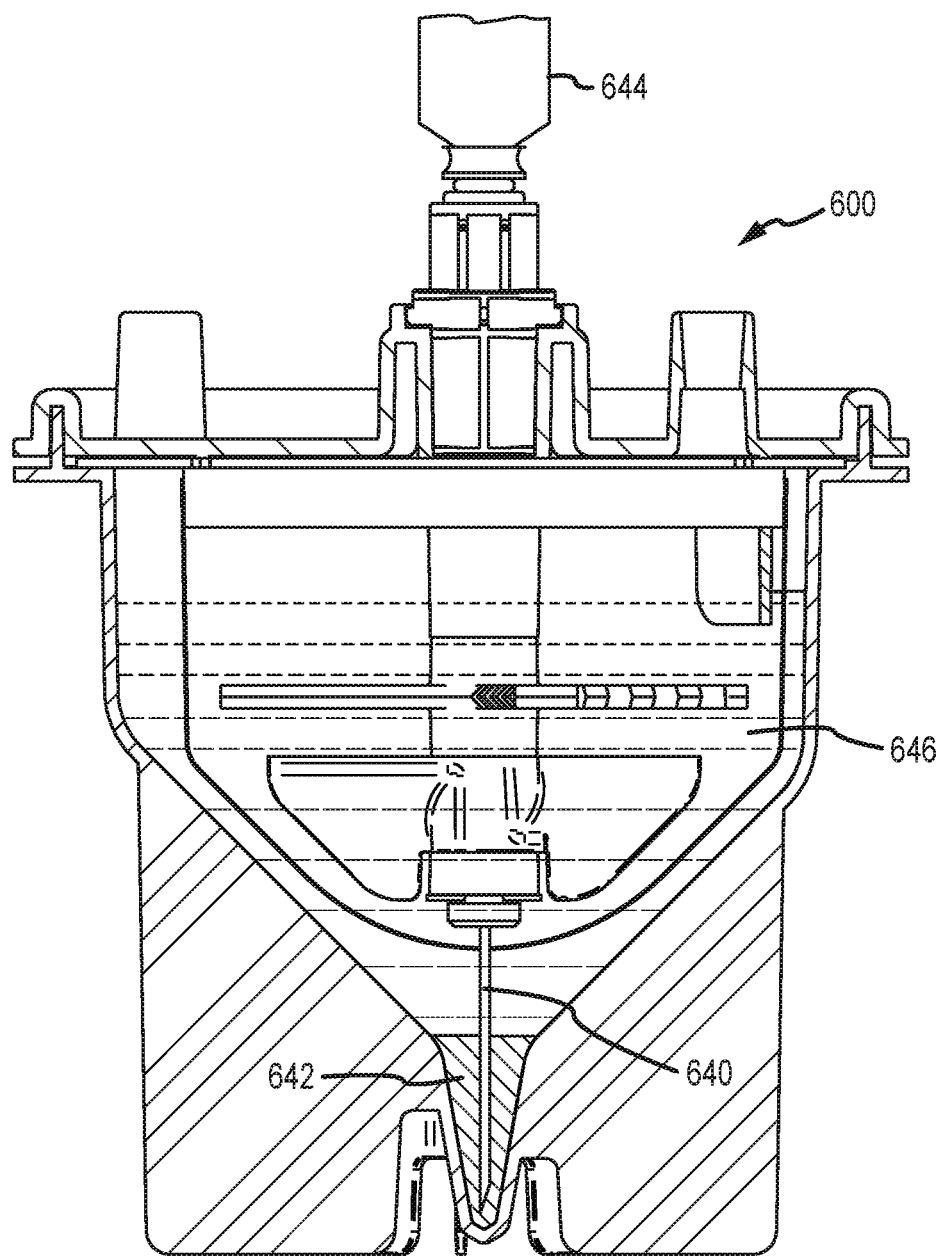
FIG. 15 shows the same embodiment of a portable container apparatus as FIG. 14 with the end of a hypodermic needle inserted into the pellet well from above for removal of material of a pellet phase from the pellet well.

The location and configuration of the pellet well 626 in the embodiment of the apparatus 600 shown in FIG. 14 facilitates direct aspiration of material of a pellet phase that may collect in the pellet well 626 by providing a relatively deep and narrow chamber that helps facilitate effective aspiration of the pellet phase material without also aspirating large quantities of overlying material from less-dense material phases that may form during centrifuge processing. FIG. 15 shows the apparatus 600 of FIG. 14 in which a hypodermic needle 640 is inserted through the lumen of the rotatable shaft to access pellet phase material 642 from above for direct aspiration of the pellet phase material 642 from the pellet well 626 through the hypodermic needle 640 to outside of the container and into a syringe 644. Such direct aspiration of the pellet phase material 642 may be performed without first removing less-dense material 646 from above the pellet phase material 642 and without suspension of the pellet phase material 642 in a suspension liquid. The syringe 644 may be preloaded with a quantity of dispersion medium that mixes with and disperses aspirated pellet phase material as it is introduced into the syringe 644. This may help prevent clumping of the pellet phase material in the syringe. The resulting mixture of pellet phase material and dispersion medium may be removed and further processed to prepare a composition for administration to a patient or the mixture may be directly administered to a patient as a delivery composition, such by injection into a patient in the vicinity of a joint, for example to treat for some condition at the joint. If a mixture in the syringe is removed from the syringe 644 for further processing, the mixture may be centrifuged to separate pellet phase material and suspension liquid and the separated pellet phase material may be recovered and formulated with other components in a delivery composition, which may for example include a scaffold material, which may be a dispersion medium with properties and at a volume desired for a particular treatment application. Any of the wall surfaces defining at least a portion of any of the first tapered portion, second tapered portion and third tapered portion may have inclined planar geometry with a constant angle of inclination, as shown in FIGS. 14 and 15 for angles $A_1$, $A_2$ and $A_3$ or may have a curved geometry with a changing angle of inclination. When such a surface has a curved geometry, the respective angle may be the angle of inclination of a line tangent to a point on the curved geometry.

Figure 16:
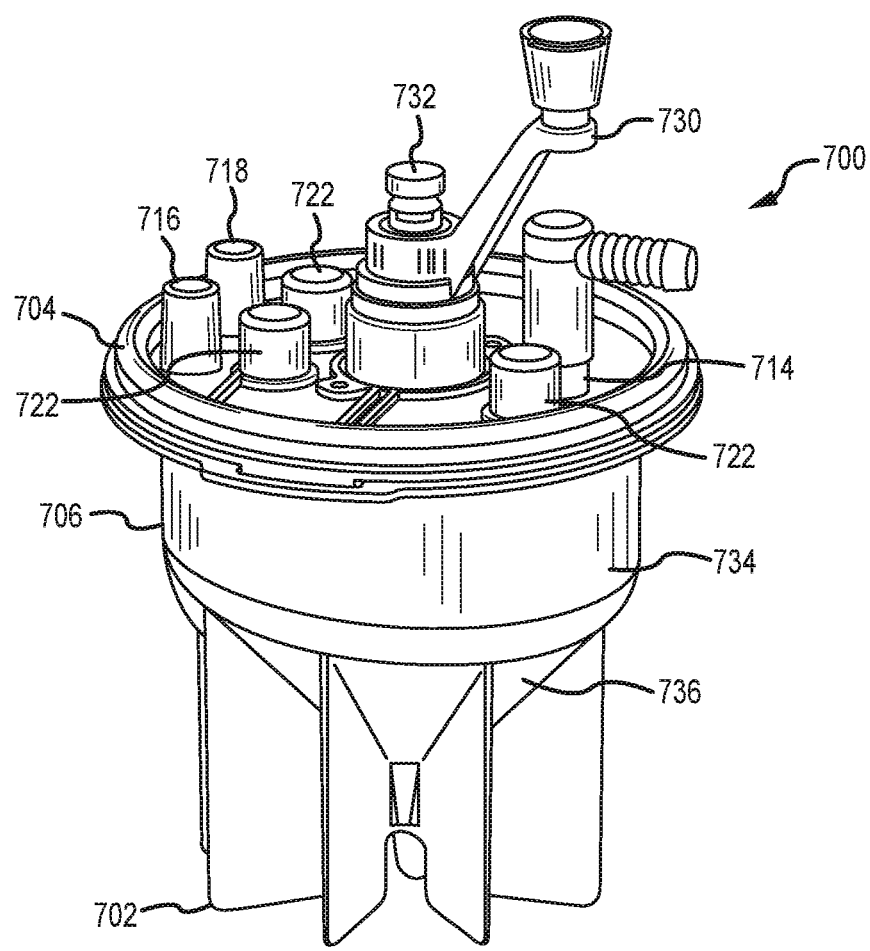
FIGS. 16-20 show another embodiment of a portable container apparatus.
Figure 17:
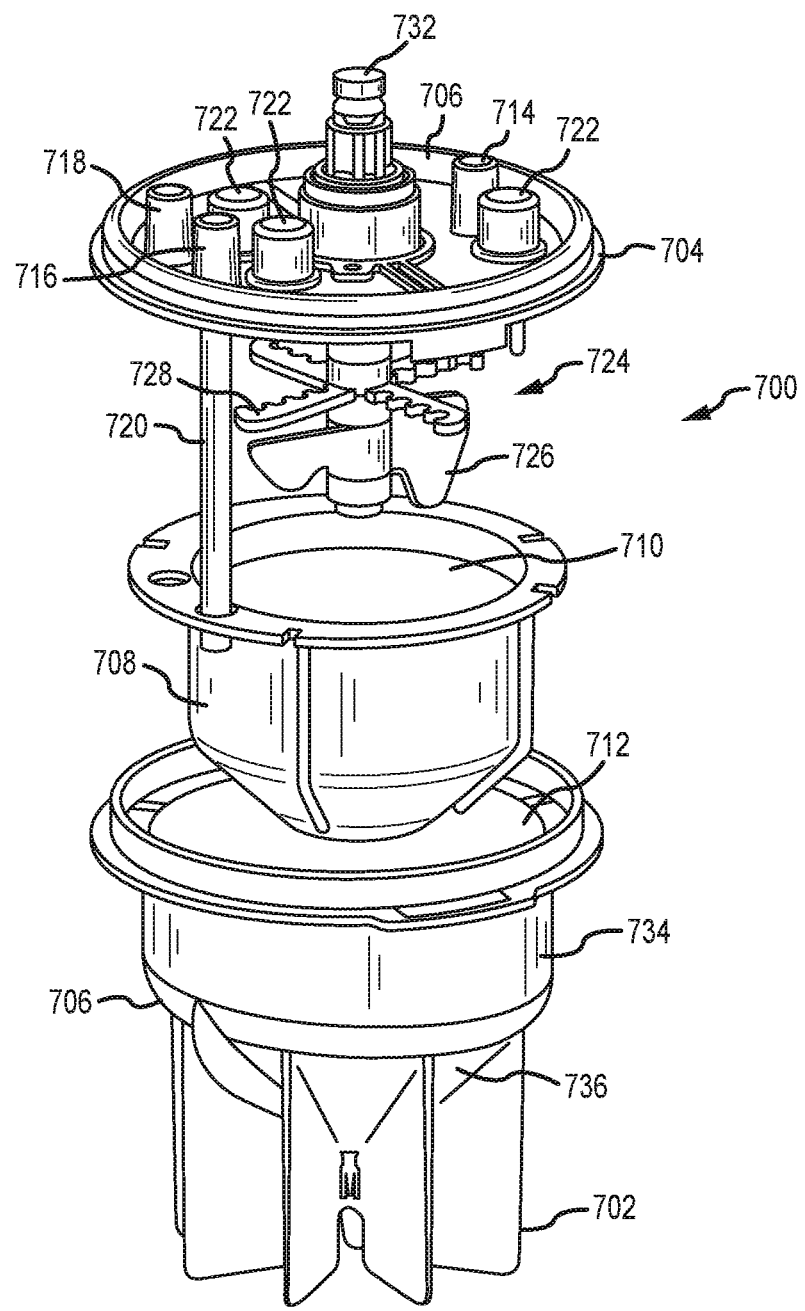

FIGS. 16 and 17 show another embodiment for a portable container apparatus. In FIGS. 16 and 17, a portable container apparatus 700 is shown in an access orientation in a free-standing, upright position as supported by base supports 702. The apparatus 700 includes a lid 704 and a bowl-like shell 706, which together make up a container having an internal containment volume within the container. A filter 708 divides the internal containment volume into a tissue retention volume 710 inside the filter 708 and a filtrate volume 712 disposed on the other side of the filter 708 between the filter 708 and the shell 706. An inlet port 714 provides access to the tissue retention volume, for example to introduce cancellous bone material into the tissue retention volume for processing. A first suction port 716 and a additional port 718 (e.g., second suction port or vent port) to provide access to the filtrate volume 712, for example to suction fluids from the filtrate volume 712. The first suction port 716 is connected with a suction conduit 720 extending from the first suction port 716 to within a tapered portion of the internal containment volume of the apparatus 700. The additional port 718 may be adapted to receive a translatable suction conduit. Caps 722 attached to the lid 706 may be used to cover the first suction port 716, additional port 718 and inlet port 714 as needed. The apparatus 700 includes a rotatable assembly 724 including a mixing impeller 726 and a tissue collector 728 mounted on a rotatable shaft. The rotatable shaft is rotatable by a hand-manipulable handle 730 (shown in FIG. 16). A lumen extends through the rotatable shaft to provide access from outside of the apparatus 700 into the internal containment volume of the apparatus. The apparatus 700 is shown fitted with a cap 732 that may be removed to permit access to the lumen through the rotatable shaft. The lid 704, shell 706, filter 708, tissue retention volume 710, filtrate volume 712, inlet port 714, first suction port 716, additional port 718, suction conduit 720, mixing impeller 726, tissue collector 728, rotatable assembly 724 and the rotatable shaft and lumen therethrough for the apparatus 700 may have any design feature or features or configurations described previously in relation to corresponding features of any apparatus described in any of FIGS. 1-15, except as specifically noted. As described previously for the tissue collector 620 of apparatus 600 shown in FIGS. 14 and 15, the tissue collector 728 of apparatus 700 may help to collect stringy tissue components that may be present to inhibit plugging of the filter 708 by such stringy tissue components. With respect to processing cancellous bone material, which typically does not contain stringy tissue components, such a tissue collector 728 may be removed from the apparatus design, although inclusion of the tissue collector 728 is not detrimental to processing cancellous bone material and provides flexibility for possible use of the apparatus 700 in a variety of different tissue processing applications, some of which may include stringy tissue components.

As distinguished from the apparatus embodiments shown in FIGS. 1-13, the apparatus 700 has a generally circular container cross-section, as opposed to the octagonal container cross-section for the apparatuses of FIGS. 1-13. The circular shape may advantageous for providing a flexible design for processing a wide range of tissue volumes and for compatibility with a variety of common centrifuges.

Figure 18:
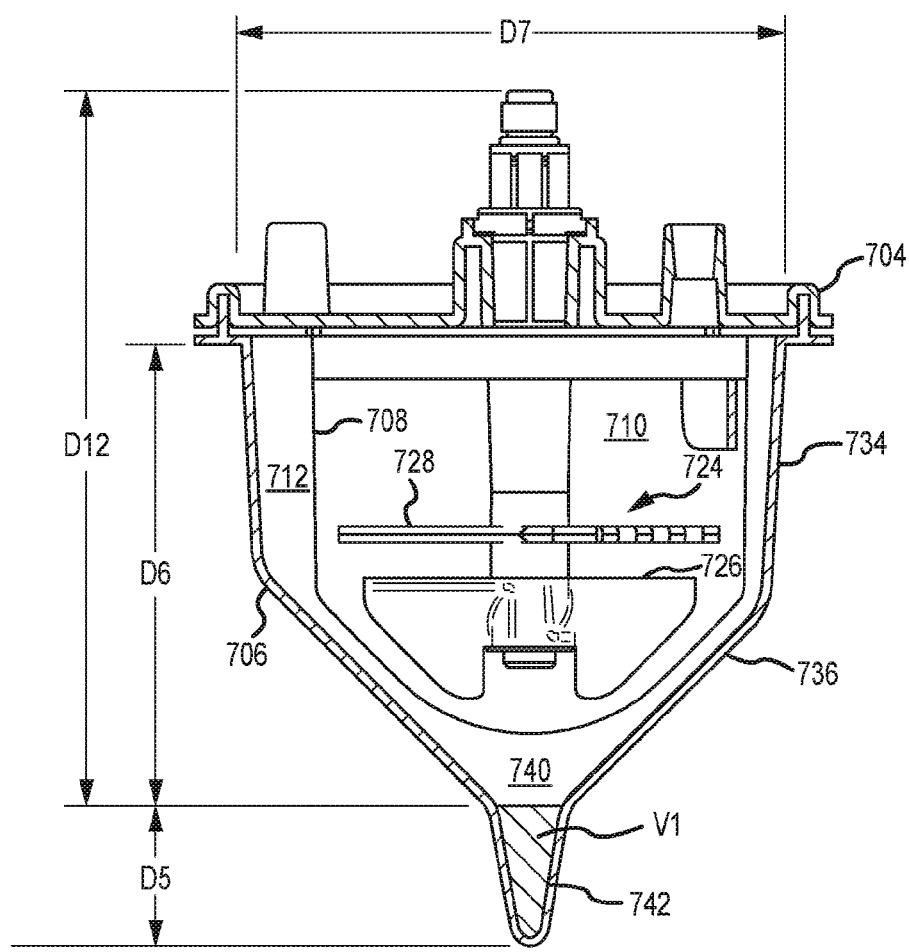
Figure 19:
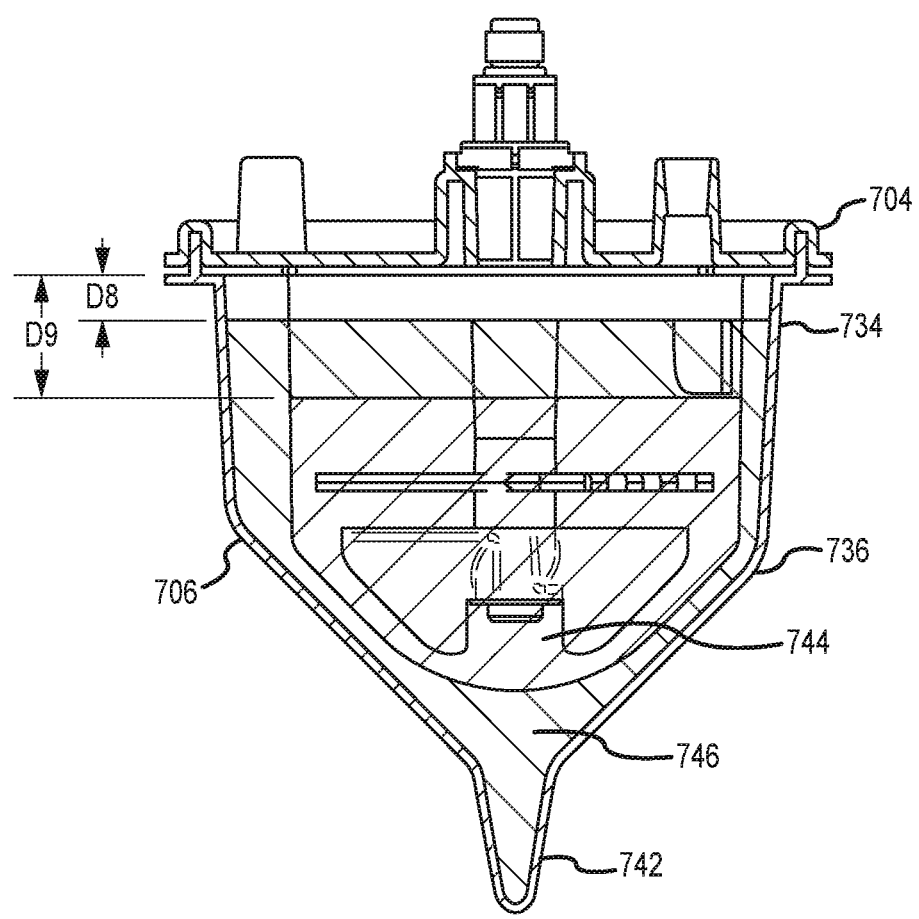
Figure 20:
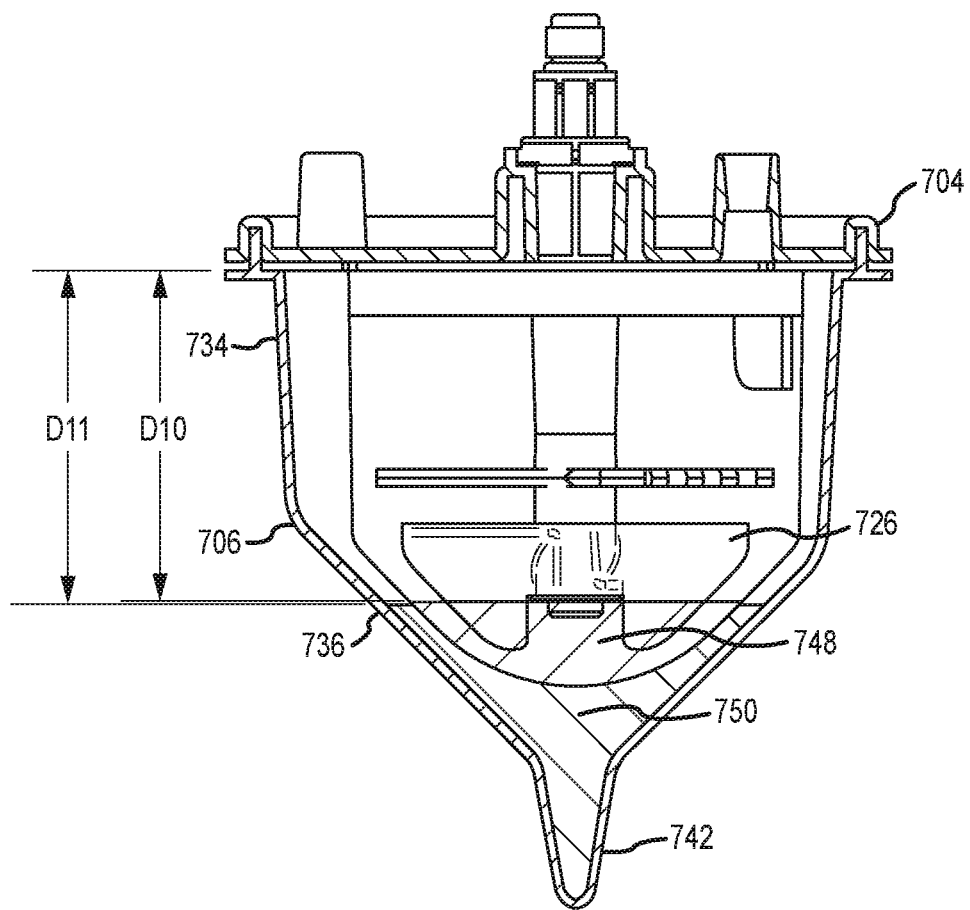

The shell 706, and the internal containment volume within the shell 706 and the lid 704, includes an first portion 734 and a second portion 736. The first portion 734 is a portion of the internal containment volume that has a substantially circular cross-section that either does not taper (e.g., is cylindrical) or that tapers only minimally. In that regard, the internal wall surface of the first portion 734 may be inclined relative to horizontal at an angle of from 70° to 90°. The second portion 736 includes a portion of the internal containment volume that tapers at a significant rate in a direction toward the bottom of the apparatus 700. The internal wall surface of the second portion 736 may be inclined relative to horizontal at an angle in a range having a lower limit of 30° to 60°, with about 45° being preferred for some implementations. The second portion 736 may taper downward toward a pellet well configured to collect pellet phase material including stromal vascular fraction cells from digested cancellous bone material. The pellet well may include a third portion of the internal containment volume that tapers in a downward direction with an internal wall surface that may be inclined relative to horizontal at an angle of from 70° to 90°. The first portion 734 may include a cylindrical shape or a frustoconical shape. The second portion 736 may each include a frustoconical shape. The third portion within the pellet well may include a cylindrical shape or a frustoconical shape. FIGS. 18-20 show an example implementation for the apparatus 700 including such a pellet well and designed for flexibility in processing a significant range of volumes of cancellous bone material.

FIG. 18 shows the lid 704 and the shell 706 of the apparatus 700 enclosing the filter 708 and the rotatable assembly 724 within an internal containment volume including the tissue retention volume 710 and the filtrate volume 712. The filtrate volume 712 includes a collection volume 740 located below a lowest elevation of the filter 708. Within the collection volume 740 is a pellet well 742 providing a volume V1 in which pellet phase material may collect during centrifuge processing of the apparatus 700 following enzymatic digestion of cancellous bone material.

FIGS. 19 and 20 illustrate flexibility of the apparatus 700 to process a wide range of cancellous bone material volumes while providing sufficient processing volume to accommodate at least an equal volume of process liquid (e.g., wash liquid or digestion medium). FIG. 19 illustrates the internal containment volume of the apparatus 700 including a large volume of cancellous bone material 744 disposed in the internal containment volume 710 and with an equal quantity of process liquid 746 (e.g., wash liquid or digestion medium) occupying the remaining portion of the available processing volume within the internal containment volume 710. FIG. 20 illustrates the internal containment volume of the apparatus 700 including a much smaller volume of cancellous bone material 748 disposed within the tissue retention volume 710 along with an equal volume of process liquid 750. As shown in FIG. 20, the combined cancellous bone material 748 and process liquid 750 fill a bottom portion of the available processing volume disposed within the second portion 736 to cover a lower tapered portion of the mixing impeller 726 for effective mixing. As will be appreciated, a smaller volume of cancellous bone material could be effectively processed than shown in FIG. 20 by increasing the amount of process liquid relative to cancellous bone material to achieve at least a similar filling of the available processing volume to cover a lower tapered portion of the mixing impeller. The volume ratio of process liquid to cancellous bone material may be much larger than 1:1. For example, a small volume of cancellous bone material (1-2 cubic centimeters) may be processed with at a volume ratio of digestion medium to cancellous bone material in excess of 10:1, in excess or 20:1 or at a even larger ratio.

The corresponding tapered features of the second portion 736 of the internal containment volume 736, the filter 708 and the mixing impeller 726 permit effective processing (e.g., washing or digesting) with mixing a very small volume of cancellous bone material, while the volume provided by the first portion 734 of the internal containment volume permits flexibility to use the same apparatus to also effectively process a much larger volume of cancellous bone material. The relatively deep and narrow profile of the pellet well permits collection of a wide range of volumes of pellet phase material resulting from processing a wide range of cancellous bone material volumes and permits effective removal of such a range of pellet phase material volumes from the pellet well, such as by direct aspiration from the pellet well without dilution and without dispersing the pellet phase material in a suspension liquid.

FIGS. 18-20 show some dimensions in relation to for the apparatus 700. D5 is a height dimension to the top of the pellet well 742. D6 is a height dimension of the internal containment volume located above the pellet well. D7 is a maximum diameter of the circular cross-section of the outside of the shell 706 configured to be received in a centrifuge bucket, below a lip at the top of the shell 706 that would ordinarily be above the top of the centrifuge bucket during centrifuging. D8 is a distance below the lid 704 to the maximum fill level in the internal containment volume for the available processing volume of the apparatus 700. D9 is a distance below the lid 704 to which the tissue retention volume 710 may be filled with cancellous bone material while still providing room for addition of process liquid in an amount of at least a 1:1 volume ratio of wash liquid to cancellous bone material. D10 is a distance below the lid 704 showing a minimum design fill volume within tissue retention volume for desired mixing by the mixing impeller 726. D11 is a distance below the lid 704 showing fill volume of process liquid in the filtrate volume when the process liquid is present at a 1:1 volume ratio to cancellous bone material corresponding with the fill level of cancellous bone material shown in FIG. 20. D12 is a total height dimension of the apparatus 700 configured to be compatible with and not interfere with operation of a centrifuge in which the apparatus is to be received during centrifuging. Some example dimensions for one example design implementation for the apparatus 700 is for D5 of about 27 millimeters, D6 of about 85 millimeters, D7 of about 100 millimeters, D8 of about 8 millimeters, D9 of about 21 millimeters, D10 of 58 about millimeters, D11 of about 58 millimeters and D12 of about 150 millimeters, and with the internal wall surface of the shell 704 defining the second portion 736 being inclined at an angle of 45° relative to horizontal. Such a design may be configured with an available processing volume of about 350 cubic centimeters that accommodates processing a range of cancellous bone material from a minimum of 20 cubic centimeters to a maximum of 175 cubic centimeters with adequate available processing volume to permit a volume ratio of cancellous bone material to wash liquid (or to digestion medium) of at least 1:1. Such a design may include a volume V1 of the pellet well 742 for example of about 1.2 cubic centimeters. The pellet well 742 may for example have a maximum diameter (maximum horizontal cross-dimension for a circular cross-section) at the top of the pellet well of about 8 millimeters.

Figure 21:
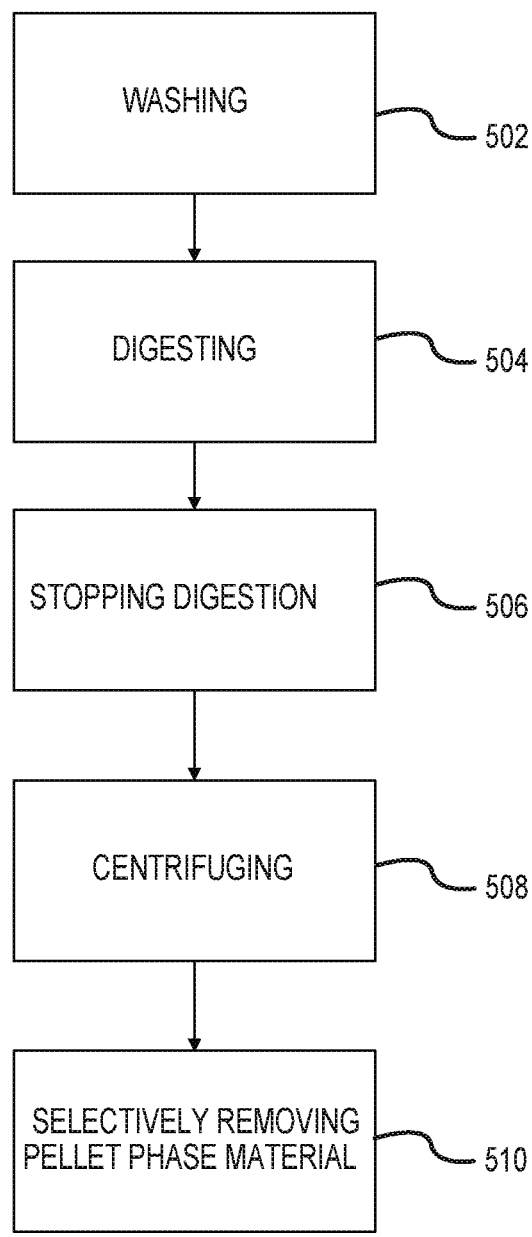
FIG. 21 is a generalized process block diagram of an embodiment of a method of processing cancellous bone material.

FIG. 21 is a generalized process block diagram illustrating one embodiment of a method involving multi-step processing within a portable container, such as for example using a tissue collection and processing apparatus as previously described. As shown in FIG. 21, the method includes a washing step 502, during which cancellous bone material disposed within a portable container apparatus is washed to remove washable components from the cancellous bone material. Washable components may include some non-bone constituents that may be associated with the cancellous bone material, for example bone marrow, blood and other blood-derived tissues and fluids.

The washing 502 may include one or multiple wash cycles during which cancellous bone material is washed with wash liquid within the portable container apparatus. The wash liquid, for example, may be a buffer solution, such as Lactated Ringer's solution or Hank's Balanced Solution, and may have additional additives, such as one or more of an anti-clotting agent, an antibiotic and an antifungal. An anti-clotting agent may beneficially prevent coagulation of blood that may be present, and may assist effective washing of blood from the cancellous bone material. Antibiotics and antifungals may help protect against problems associated with inadvertent outside contamination of the cancellous bone material within the portable container apparatus. Such a wash liquid may also include one or more additional buffering agents, such as glycine. One preferred material for use as an anti-clotting agent is heparin.

During a wash cycle, the wash liquid is mixed with the cancellous bone material in the portable container apparatus and then preferably substantially all of the wash liquid with washed components from the cancellous bone material is removed from the portable container apparatus from a filtrate volume on a first side (filtrate side) of a filter within the container while retaining the washed cancellous bone material in a retentate volume of the container on a second side (retentate side) of the filter.

The washing may include any of the feature refinements and additional features discussed above.

After the washing 502, the washed cancellous bone material in the portable container apparatus is subjected to a digesting step 504. Digestion medium, such as comprising a collagenase enzyme solution is added to the portable container apparatus to contact washed cancellous bone material. The digestion medium may contain collagenase enzyme in an amount to provide preferably from 100 to 300 collagen digestion units (CDU) per milliliter of catalytic volume. Catalytic volume refers to the total volume of the digestion medium and cancellous bone material within the portable container apparatus to which the digestion medium is added. After the digestion medium is added to the portable container apparatus, enzymatic digestion within the portable container apparatus is permitted to proceed for a retention time preferably in a range of from 20 minutes to 60 minutes while the portable container apparatus is disposed in a temperature controlled environment maintained within a temperature range of from 32° C. to 38° C. (preferably at least 34°), and with at least occasional, and preferably substantially continuous, agitation of contents to the portable container apparatus. The digesting step 504 may include any of the feature refinements and additional features discussed above.

The method as shown in FIG. 21 also includes a stopping digestion step 506 occurring after the digesting step 504. The stopping digestion step 506 should preferably occur no earlier than the end of the retention time for the enzymatic digestion in the temperature controlled environment, and more preferably within 60 minutes following adding the digestion medium to the portable container apparatus during the digesting step 504. The stopping digestion step 506 may include adding a stopping reagent to the portable container apparatus to positively stop enzymatic activity of the digestion medium within the portable container apparatus. This is important, because if enzymatic activity is not discontinued, digestion within the portable container apparatus may proceed to an undesirable degree in which the enzyme may destroy the viability of a significant number of the stromal vascular fraction cells.

As shown in FIG. 21, the method includes, after the stopping digestion step 506, a centrifuging step 508. The centrifuging step 508 is performed with the portable container apparatus disposed in a centrifuge and the centrifuge is operated to centrifuge the portable container apparatus to form density-separated phases within the portable container apparatus. These density-separated phases include a higher-density pellet phase rich in stromal vascular fraction cells, which pellet phase may form adjacent a bottom of the portable container apparatus. The density-separated phases also include lower-density material phases. By lower-density, it is meant that the lower-density material phases have a lower-density than the pellet phase. When the portable container apparatus is oriented with the pellet phase adjacent a bottom of the filtrate volume (e.g., in an access orientation for the portable container apparatus), the lower-density material phases will be disposed in the portable container apparatus above the pellet phase. The lower-density material phases may include for example, one or more of the material phases as described previously. The pellet phase is enriched in, and may be mostly or even substantially entirely comprised of, stromal vascular fraction cells. On a side of the pellet phase opposite the lower-density material phases may be disposed a small red blood cell phase, as discussed above. Provided that washing of the cancellous bone material is thorough during the washing step 502, this red blood cell phase may be extremely small, and in some case may be difficult to distinguish from a bottom portion of the pellet phase. The centrifuging step 508 may include any of the feature refinements and additional features discussed above.

As shown in FIG. 21, the stopping digestion step 506 is performed after the digesting step 504 and prior to the centrifuging step 508. Such sequencing is preferred, but not required. In one variation, the stopping digestion step 506 may be performed after the centrifuging 508. However, because enzymatic digestion would continue during the centrifuging, such a variation in the sequence is not preferred, to provide better control over the timing and extent of the enzymatic digestion.

After the centrifuging step 508 has been completed, the container may be removed from the centrifuge and subjected to a step 510 of selectively removing pellet phase material. The stromal vascular fraction cells, which include stem cells, contained in the pellet phase represent valuable product. For effective use of these valuable stromal vascular fraction cells, it is generally necessary to remove the cells from the portable container apparatus. During the step 510, material of the pellet phase is removed from the internal containment volume of the container to outside of the container separate from the less-dense material phases. The step 510 may include any of the features as discussed above. In some processing alternatives, the pellet phase material may be directly aspirated through an aspiration tube (e.g., hypodermic needle) inserted into the pellet phase from above and material of the pellet phase may be directly aspirated from the container through the aspiration tube, for example into a syringe or other fluid receptacle located outside of the container.

Figure 22:
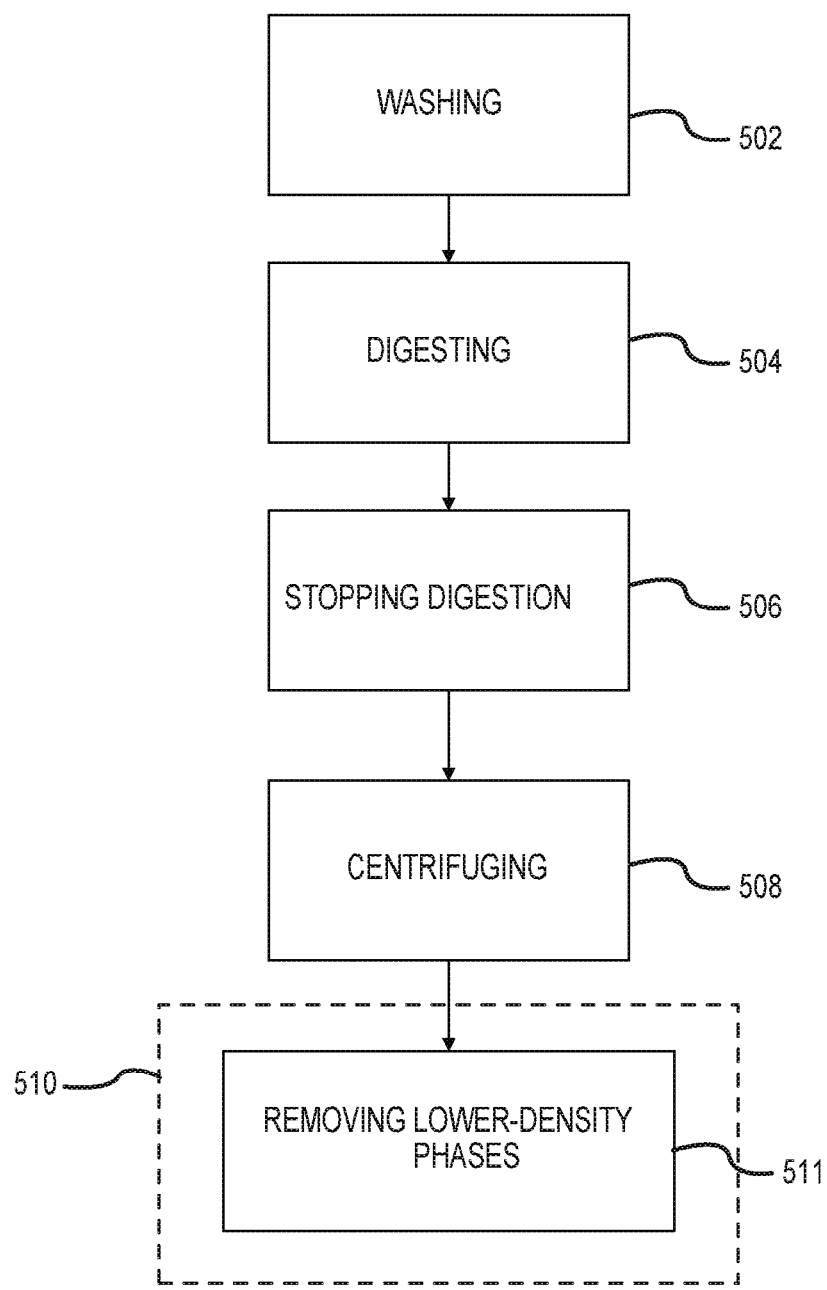
FIG. 22 is a generalized process block diagram of another embodiment of a method of processing cancellous bone material.
Figure 23:
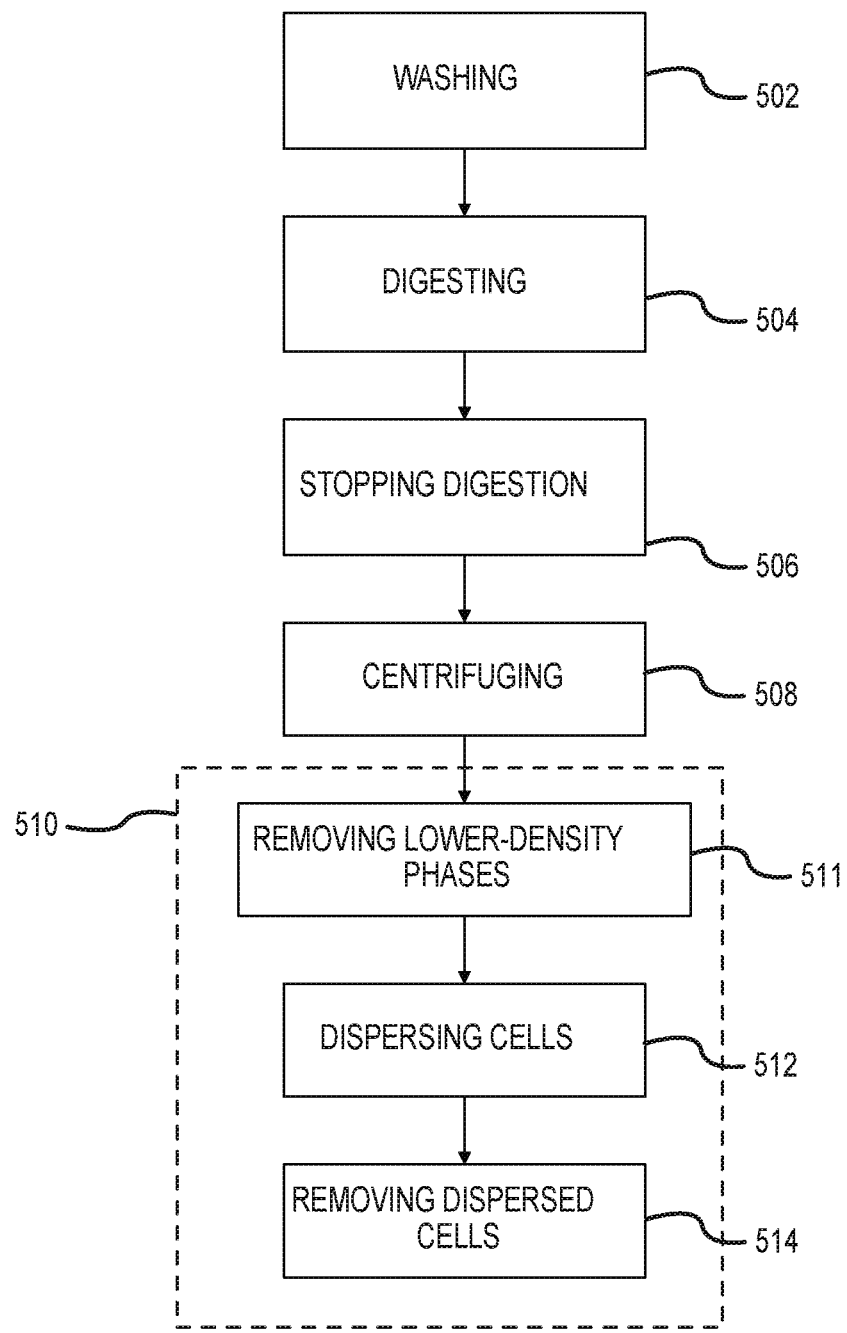
FIG. 23 is a generalized process block diagram of another embodiment of a method of processing cancellous bone material.

Referring now to FIG. 22, another embodiment of implementation of a method is shown, including an alternative approach for selectively removing material of the pellet phase from the container. The implementation shown in FIG. 22 includes the washing step 502, the digesting step 504, the stopping digestion step 506, the centrifuging step 508 and the selectively removing pellet phase material step 510 as discussed with FIG. 21. As shown in FIG. 22, the step 510 includes steps 511, 512 and 514. During the step 511, the lower-density material phases formed during centrifuging may be removed from the container while the pellet phase is retained within the container, preferably while maintaining the pellet phase in an undisturbed state at the location of the container where the pellet collected during the centrifuging. The step 511 may include any or any combination of the features as discussed above. FIG. 23 shows a more specific implementation in which after the removing lower-density phases step 511, the step 510 includes a dispersing cells step 512. During the dispersing cells step 512, aqueous suspension liquid is introduced into the portable container apparatus to mix with the pellet phase and to act as a dispersion medium for dispersing cells of the pellet phase in the suspension liquid. Dispersion of cells from the pellet phase may be aided by tapping the portable container apparatus to dislodge and break up the pellet phase to assist effective dispersion of the leuko stromal vascular cells in the suspension liquid. The dispersing cells step 512 may include any of the features as discussed above.

After the dispersing cells step 512, the processing shown in FIG. 23 includes a removing dispersed cells step 514, during which most, and preferably substantially all, of the suspension liquid with the dispersed cells from the pellet phase is removed from the portable container apparatus, thereby recovering the stromal vascular fraction cells from the portable container apparatus. The removing dispersed cells step 514 may include any of the features discussed above.

As another alternative to the processing for the selectively removing pellet phase material step 510 shown in FIG. 23, after the removing lower-density material phases step 511, the material of the pellet phase could be removed from the container by direct aspiration through an aspiration tube, such as a hypodermic needle. With this processing alternative, the cells of the pellet phase material would not be dispersed or suspended in a suspension liquid prior to removal from the container.

The method of the disclosure includes multi-step processing in a single portable container apparatus, such as for example the portable container apparatus as described above. The method is designed to address inherent problems with multi-step processing in a single container.

Figure 24:
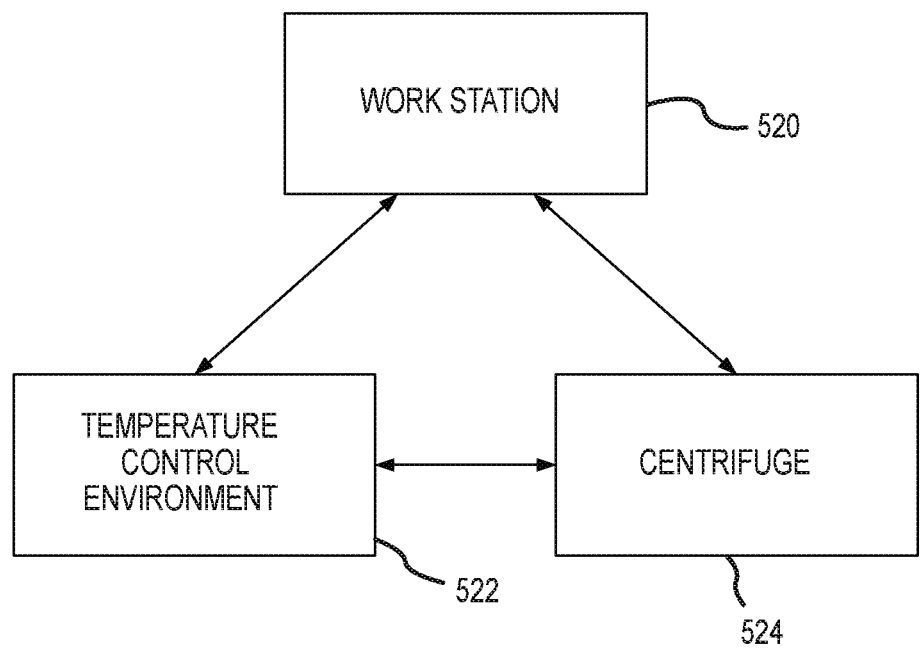
FIG. 24 illustrates transportability of a portable container apparatus to accommodate performing different processing operations at different locations.

Reference is now made to FIG. 24, which illustrates portability of the portable container apparatus during implementation of a method of the disclosure. As shown in FIG. 24, processing may be performed at a facility providing multiple distinct locations where the portable container apparatus may be temporarily located to perform different processing operations within the portable container apparatus. FIG. 24 shows three such possible distinct processing locations: a work station, a centrifuge and a temperature controlled environment. As shown by the arrows in FIG. 24, the portable container apparatus may be transported between these different locations to perform different process tasks or operations, for example processing tasks and operations associated with the method implementations of FIGS. 21-23. The transportation may conveniently be accomplished by a person carrying the portable container apparatus between the different locations.

The work station 520 may include a flat work surface, such as a flat surface of a table, bench or counter where the portable container apparatus may be stably positioned in an access orientation for convenient access to add material to or remove material from the portable container apparatus. In a preferred implementation, when the portable container apparatus is in such an access orientation, all access into the container apparatus for adding and removing materials is in a downward direction from above the container apparatus. Operations that may be performed at such a work station 520 include, for example, one or more of the washing step 502, the stopping digestion step 506, the removing lower-density phases step 511, the dispersing cells step 512, and the removing dispersed cells step 514 shown in FIGS. 21-23. Adding digesting medium to the portable container apparatus may also be conveniently performed at such a work station 520. As will be appreciated, an actual facility may include multiple work stations, rather than a single work station as shown in FIG. 24. For example different work stations may be specifically designed and equipped for performing specific processing tasks. Such multiple work stations may be contiguous or at separated locations in a facility.

Enzymatic digestion within the portable container apparatus for a retention time may be performed at the temperature controlled environment 522. The temperature controlled environment may be provided by a warmer-shaker, for example.

Centrifuging (e.g., step 508 of FIGS. 21-23) may be performed at the location of the centrifuge 524 shown in FIG. 24.

The foregoing discussion of the disclosure and different aspects thereof has been presented for purposes of illustration and description. The foregoing is not intended to limit the disclosure to only the form or forms specifically disclosed herein. Consequently, variations and modifications commensurate with the above teachings, and the skill or knowledge of the relevant art, are within the scope of the present disclosure. The embodiments described hereinabove are further intended to explain best modes known for practicing the disclosure and to enable others skilled in the art to utilize the disclosure in such, or other, embodiments and with various modifications required by the particular applications or uses of the present disclosure. It is intended that the appended claims be construed to include alternative embodiments to the extent permitted by the prior art. Although the description of the disclosure has included description of one or more possible implementations and certain variations and modifications, other variations and modifications are within the scope of the disclosure, e.g., as may be within the skill and knowledge of those in the art after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. Furthermore, any feature described or claimed with respect to any disclosed implementation may be combined in any combination with one or more of any other features of any other implementation or implementations, to the extent that the features are not necessarily technically compatible, and all such combinations are within the scope of the present disclosure.

The terms "comprising", "containing", "including" and "having", and grammatical variations of those terms, are intended to be inclusive and nonlimiting in that the use of such terms indicates the presence of some condition or feature, but not to the exclusion of the presence also of any other condition or feature. The use of the terms "comprising", "containing", "including" and "having", and grammatical variations of those terms in referring to the presence of one or more components, subcomponents or materials, also include and is intended to disclose the more specific embodiments in which the term "comprising", "containing", "including" or "having" (or the variation of such term) as the case may be, is replaced by any of the narrower terms "consisting essentially of" or "consisting of" or "consisting of only" (or the appropriate grammatical variation of such narrower terms). For example, the a statement that some thing "comprises" a stated element or elements is also intended to include and disclose the more specific narrower embodiments of the thing "consisting essentially of" the stated element or elements, and the thing "consisting of" the stated element or elements. Examples of various features have been provided for purposes of illustration, and the terms "example", "for example" and the like indicate illustrative examples that are not limiting and are not to be construed or interpreted as limiting a feature or features to any particular example. The term "at least" followed by a number (e.g., "at least one") means that number or more than that number. The term at "at least a portion" means all or a portion that is less than all. The term "at least a part" means all or a part that is less than all.

What is claimed is:

1. A method for processing cancellous bone material initially comprising cancellous bone and associated blood, the method comprising;
    performing processing operations using a portable container apparatus;
    the portable container apparatus having a filter disposed in an internal containment volume of the portable container apparatus and the internal containment volume includes a retentate volume on one side of the filter and a filtrate volume on another side of the filter;
    the processing operations comprising:
        washing, wherein the washing comprises adding aqueous wash liquid to the portable container apparatus to contact cancellous bone material disposed within the retentate volume and removing from the filtrate volume at least a majority of the aqueous wash liquid together with at least some blood washed from the cancellous bone material;
        after the washing, digesting, wherein the digesting comprises adding to the portable container apparatus a digestion medium comprising collagenase enzyme to contact the digestion medium with at least a washed portion of the cancellous bone material disposed in the retentate volume; and
        after the digesting, centrifuging the portable container apparatus having disposed within the internal containment volume at least a digested portion of the cancellous bone material, and during the centrifuging forming in the internal containment volume density-separated phases, the density-separated phases including lower-density material phases and a higher-density pellet phase concentrated in stromal vascular fraction cells from the cancellous bone material;
    and wherein:
        the apparatus has an access orientation;
        the internal containment volume includes a pellet well disposed in a bottom portion of the filtrate volume below a bottom elevation of the filter and accessible only from above when the apparatus is in the access orientation;
        the filtrate volume includes a lower tapered portion below a bottom elevation of the filter and above a top elevation of the pellet well;
        the lower tapered portion of the filtrate volume is defined by internal wall surfaces of the container that are inclined relative to horizontal at a maximum angle of no larger than 60° when the container is in the access orientation; and
        at least a portion of the pellet well is defined by a wall surface of the container inclined relative to horizontal at an angle that is larger than the maximum angle of the lower tapered portion when the apparatus is in the access orientation.

2. The method according to claim 1, comprising after the centrifuging, selectively removing material of the pellet phase from the portable container apparatus.

3. The method according to claim 2, wherein the selectively removing comprises:
    inserting an aspiration tube from outside of to inside of the portable container apparatus to contact the pellet phase inside the portable container apparatus; and aspirating at least a majority of material of the pellet phase through the aspiration tube to outside of the portable container apparatus.

4. The method according to claim 3, wherein:
the aspirating comprises aspirating the at least a majority of the material of the pellet phase into a receptacle located outside of the portable container apparatus that is in fluid communication with the aspiration tube; and
prior to commencement of the aspirating, the receptacle contains a volume of dispersion medium and during the aspirating the dispersion medium mixes with the at least a majority of the material of the pellet phase in the receptacle; and
the volume of the dispersion medium is in a range of from 2 times to 10 times a volume of the at least a majority of the material of the pellet phase that is aspirated into the receptacle during the aspirating.

5. The method according to claim 4, wherein during the aspirating the aspiration tube is in fluid communication with a syringe and the aspirating comprises collecting the at least a majority of the material of the pellet phase in the syringe.

6. The method according to claim 1, wherein:
the digesting comprises adding to the portable container apparatus a volume of the digestion medium that provides from 100 to 300 collagen digestion units (CDU) per milliliter of catalytic volume, wherein the catalytic volume is the total of the volume of digestion medium and the volume of the at least a washed portion of the cancellous bone material within the retentate volume;
the digestion medium is within a temperature range of from 32° C. to 38° C. when the digestion medium is added to the portable container apparatus; and
the digesting comprises after the adding digestion medium, permitting enzymatic digestion within the portable container apparatus for a retention time in a range of from 20 minutes to 60 minutes.

7. The method according to claim 6, wherein:
during the retention time the portable container apparatus is disposed in a temperature controlled environment maintained within a temperature range of from 32° C. to 38° C.; and
the retention time is in a range of from 25 minutes to 45 minutes.

8. The method according to claim 1, wherein the internal containment volume has an internal processing volume in a range of from 25 cubic centimeters to 400 cubic centimeters.

9. The method according to claim 1, wherein the wall surface of the container defining at least a portion of the pellet well is inclined relative to horizontal at an angle of at least 70° when the apparatus is in the access orientation.

10. The method according to claim 9, wherein:
when the apparatus is in the access orientation, the pellet well has at least one portion with a vertical length of at least 0.5 centimeter, a maximum horizontal cross-dimension of no larger than 10 millimeters and a minimum horizontal cross-dimension of no smaller than 1.5 millimeters.

11. The method according to claim 10, wherein the pellet well has a volume in a range of from 0.3 cubic centimeter to 3 cubic centimeters.

12. The method according to claim 11, wherein the pellet well includes a frustoconical portion with an angle of taper relative to horizontal of at least 70° when the container is in the access orientation.

13. The method according to claim 11, comprising removing material of the pellet phase from the portable container apparatus by direct aspiration from the pellet well through an aspiration tube inserted into the pellet into the pellet phase in the pellet well.

14. The method according to claim 11, wherein:
the lower tapered portion is a first tapered portion and the pellet well includes a second tapered portion of the internal containment volume that has a greater rate of taper than the first tapered portion; and
the internal containment volume includes an available processing volume and the second tapered portion has a volume that is in a range of from 0.2 percent to 2.5 percent of a portion of the available processing volume that is within the retentate volume.

15. The method according to claim 14, wherein the available processing volume is in a range from 25 cubic centimeters to 300 cubic centimeters.

16. The method according to claim 1, wherein when the portable container apparatus is in the access orientation the internal containment volume comprises:
a first portion that is cylindrical or is frustoconical tapering toward the bottom of the internal containment volume with an angle of taper relative to horizontal of at least 70°;
a second portion disposed below the first portion, the second portion being frustoconical tapering toward the bottom of the internal containment volume with an angle of taper relative to horizontal in a range of from 30° to 60°;
a third portion disposed below the second portion in the pellet well, the third portion being cylindrical or frustoconical tapering toward the bottom of the internal containment volume at an angle of taper relative to horizontal of at least 70°.

17. The method according to claim 1, comprising:
preparing a medical treatment composition for administration to a human, the preparing a medical treatment composition comprising mixing, outside of the portable container apparatus, a biocompatible scaffold material with at least a portion of the stromal vascular fraction cells from the pellet phase.

18. The method according to claim 1, wherein the filter has a separation size in a range of from 70 microns to 250 microns.

* * * * *